(12) United States Patent
Sikiric et al.

(10) Patent No.: US 6,288,028 B1
(45) Date of Patent: Sep. 11, 2001

(54) BPC PEPTIDE SALTS WITH ORGANO-PROTECTIVE ACTIVITY, THE PROCESS FOR THEIR PREPARATION AND THEIR USE IN THERAPY

(76) Inventors: Predrag Sikiric, Jurisiceva 5; Marijan Petek, Visnjica 29; Sven Seiwerth, Palmoticeva 17; Branko Turkovic, Bauerova 18; Zeljko Grabarevic, Mikulic Odvojak 7; Ivo Rotkvic, Cvjetno Naselje 21, all of HR-41000 Zagreb; Stjepan Mise, Roosveltova 37, HR-58000 Split; Marko Duvnjak, Meduliceva 18B, HR-41000 Zagreb, all of (HR); Ivan Udovicic, Ennetmooserstrasse 16, CH-6370 Stans-NW (CH)

( * ) Notice: Subject to any disclaimer, the term of this patent is extended or adjusted under 35 U.S.C. 154(b) by 0 days.

(21) Appl. No.: 09/424,414
(22) PCT Filed: May 20, 1998
(86) PCT No.: PCT/EP98/02953
    § 371 Date: Feb. 15, 2000
    § 102(e) Date: Feb. 15, 2000
(87) PCT Pub. No.: WO98/52973
    PCT Pub. Date: Nov. 26, 1998

(30) Foreign Application Priority Data

May 23, 1997 (EP) .................................. 97108384

(51) Int. Cl.[7] .......................... A61K 31/70; A61K 38/16; C07H 17/08; C07K 9/00
(52) U.S. Cl. .................................. 514/8; 514/8; 514/23; 514/53; 530/322; 536/7.1; 536/7.2; 536/13.8
(58) Field of Search .............................. 514/2, 8, 23, 53; 530/322, 328, 326; 536/7.1, 7.2, 13.8; 424/1.69, 1.11, 1.65

(56) References Cited

FOREIGN PATENT DOCUMENTS

| 0572688 | 8/1993 | (EP) . |
| 94 11394 | 5/1994 | (WO) . |

*Primary Examiner*—Karen Cochrane Carlson
*Assistant Examiner*—Patricia Robinson
(74) *Attorney, Agent, or Firm*—Ostrolenk, Faber, Gerb & Soffen, LLP

(57) ABSTRACT

The present invention discloses new pharmaceutical compositions useful for the treatment of various human and animal diseases. These pharmaceutical compositions contain one or more peptides.

29 Claims, 4 Drawing Sheets

SEQUENCE LISTING

```
<160> NUMBER OF SEQ ID NOS:  14

<210> SEQ ID NO 1
<211> LENGTH: 8
<212> TYPE: PRT
<213> ORGANISM: Artificial Sequence
<220> FEATURE:
<223> OTHER INFORMATION: Synthesis
<221> NAME/KEY: UNSURE
<222> LOCATION: (1)
<223> OTHER INFORMATION: Xaa is an acidic amino acid
<221> NAME/KEY: UNSURE
<222> LOCATION: (5)
<223> OTHER INFORMATION: Xaa is a neutral aliphatic amino acid
<221> NAME/KEY: UNSURE
<222> LOCATION: (6)
<223> OTHER INFORMATION: Xaa is a basic amino acid

<400> SEQUENCE: 1

Xaa Pro Pro Pro Xaa Xaa Pro Ala
 1               5
```

```
<210> SEQ ID NO 2
<211> LENGTH: 15
<212> TYPE: PRT
<213> ORGANISM: Artificial Sequence
<220> FEATURE:
<223> OTHER INFORMATION: Synthesis
<221> NAME/KEY: UNSURE
<222> LOCATION: (1)
<223> OTHER INFORMATION: Xaa is a neutral aliphatic amino acid
<221> NAME/KEY: UNSURE
<222> LOCATION: (2)
<223> OTHER INFORMATION: Xaa is an acidic amino acid
<221> NAME/KEY: UNSURE
<222> LOCATION: (6)
<223> OTHER INFORMATION: Xaa is a neutral aliphatic amino acid
<221> NAME/KEY: UNSURE
<222> LOCATION: (7)
<223> OTHER INFORMATION: Xaa is a basic amino acid
<221> NAME/KEY: UNSURE
<222> LOCATION: (11)
<223> OTHER INFORMATION: Xaa is an acidic amino acid
<221> NAME/KEY: UNSURE
<222> LOCATION: (13)..(15)
<223> OTHER INFORMATION: Xaa is a neutral aliphatic amino acid

<400> SEQUENCE: 2

Xaa Xaa Pro Pro Pro Xaa Xaa Pro Ala Asp Xaa Ala Xaa Xaa Xaa
 1               5                  10                  15

<210> SEQ ID NO 3
<211> LENGTH: 15
<212> TYPE: PRT
<213> ORGANISM: Artificial Sequence
<220> FEATURE:
<223> OTHER INFORMATION: Description of Artificial Sequence: Body
      Protective Compound Peptide or a Peptide of
      Gastric Juice Protein

<400> SEQUENCE: 3

Leu Glu Pro Pro Pro Gly Lys Pro Ala Asp Asp Ala Leu Gly Val
 1               5                  10                  15

<210> SEQ ID NO 4
<211> LENGTH: 15
<212> TYPE: PRT
<213> ORGANISM: Artificial Sequence
<220> FEATURE:
<223> OTHER INFORMATION: Description of Artificial Sequence: Body
      Protective Compound Peptide or a Peptide of
      Gastric Juice Protein

<400> SEQUENCE: 4

Gly Glu Pro Pro Pro Gly Lys Pro Ala Asp Asp Ala Gly Leu Val
 1               5                  10                  15

<210> SEQ ID NO 5
<211> LENGTH: 15
<212> TYPE: PRT
<213> ORGANISM: Artificial Sequence
<220> FEATURE:
<223> OTHER INFORMATION: Description of Artificial Sequence: Body
      Protective Compound Peptide or a Peptide of
      Gastric Juice Protein

<400> SEQUENCE: 5

Leu Glu Pro Pro Pro Leu Lys Pro Ala Asp Asp Ala Leu Gly Val
 1               5                  10                  15

<210> SEQ ID NO 6
```

```
<211> LENGTH: 14
<212> TYPE: PRT
<213> ORGANISM: Artificial Sequence
<220> FEATURE:
<223> OTHER INFORMATION: Description of Artificial Sequence: Body
      Protective Compound Peptide or a Peptide of
      Gastric Juice Protein

<400> SEQUENCE: 6

Leu Glu Pro Pro Pro Leu Lys Pro Ala Asp Ala Leu Gly Val
  1               5                  10

<210> SEQ ID NO 7
<211> LENGTH: 14
<212> TYPE: PRT
<213> ORGANISM: Artificial Sequence
<220> FEATURE:
<223> OTHER INFORMATION: Description of Artificial Sequence: Body
      Protective Compound Peptide or a Peptide of
      Gastric Juice Protein

<400> SEQUENCE: 7

Gly Glu Pro Pro Pro Gly Lys Pro Ala Asp Ala Gly Leu Val
  1               5                  10

<210> SEQ ID NO 8
<211> LENGTH: 8
<212> TYPE: PRT
<213> ORGANISM: Artificial Sequence
<220> FEATURE:
<223> OTHER INFORMATION: Description of Artificial Sequence: Body
      Protective Compound Peptide or a Peptide of
      Gastric Juice Protein

<400> SEQUENCE: 8

Glu Pro Pro Pro Leu Lys Pro Ala
  1               5

<210> SEQ ID NO 9
<211> LENGTH: 9
<212> TYPE: PRT
<213> ORGANISM: Artificial Sequence
<220> FEATURE:
<223> OTHER INFORMATION: Description of Artificial Sequence: Body
      Protective Compound Peptide or a Peptide of
      Gastric Juice Protein

<400> SEQUENCE: 9

Asp Pro Pro Pro Ile Arg Pro Ala Asp
  1               5

<210> SEQ ID NO 10
<211> LENGTH: 9
<212> TYPE: PRT
<213> ORGANISM: Artificial Sequence
<220> FEATURE:
<223> OTHER INFORMATION: Description of Artificial Sequence: Body
      Protective Compound Peptide or a Peptide of
      Gastric Juice Protein

<400> SEQUENCE: 10

Glu Pro Pro Pro Leu Lys Pro Ala Asp
  1               5

<210> SEQ ID NO 11
<211> LENGTH: 14
<212> TYPE: PRT
<213> ORGANISM: Artificial Sequence
<220> FEATURE:
```

```
<223> OTHER INFORMATION: Description of Artificial Sequence: Body
      Protective Compound Peptide or a Peptide of
      Gastric Juice Protein

<400> SEQUENCE: 11

Leu Glu Pro Pro Leu Lys Pro Ala Asp Ala Leu Gly Val
 1               5                  10

<210> SEQ ID NO 12
<211> LENGTH: 10
<212> TYPE: PRT
<213> ORGANISM: Artificial Sequence
<220> FEATURE:
<223> OTHER INFORMATION: Description of Artificial Sequence: Body
      Protective Compound Peptide or a Peptide of
      Gastric Juice Protein

<400> SEQUENCE: 12

Gly Glu Pro Pro Pro Gly Arg Pro Ala Asp
 1               5                  10

<210> SEQ ID NO 13
<211> LENGTH: 9
<212> TYPE: PRT
<213> ORGANISM: Artificial Sequence
<220> FEATURE:
<223> OTHER INFORMATION: Description of Artificial Sequence: Body
      Protective Compound Peptide or a Peptide of
      Gastric Juice Protein

<400> SEQUENCE: 13

Glu Pro Pro Pro Leu Lys Pro Ala Asn
 1               5

<210> SEQ ID NO 14
<211> LENGTH: 15
<212> TYPE: PRT
<213> ORGANISM: Artificial Sequence
<220> FEATURE:
<223> OTHER INFORMATION: Description of Artificial Sequence: Body
      Protective Compound Peptide or a Peptide of
      Gastric Juice Protein

<400> SEQUENCE: 14

Gly Glu Pro Pro Pro Gly Lys Pro Ala Asp Asp Ala Gly Leu Val
 1               5                  10                  15
```

BPC PEPTIDE SALTS WITH ORGANO-PROTECTIVE ACTIVITY, THE PROCESS FOR THEIR PREPARATION AND THEIR USE IN THERAPY

BACKGROUND OF THE INVENTION

1. Field of the Invention

The present invention relates to new application forms of synthetic BPC (Body Protection Compound) peptides comprising 8 to 15 amino acid residues with a molecular weight of 900 to 1,600 daltons, which have organo-protective activity, to processes for their preparation and their use in diagnosis and therapy.

2. Description of the Related Art

Proteins and peptides which are useful for the treatment of various diseases in humans and animals are known. Many of these agents are produced in vivo and may be extracted from animals or humans to prepare pharmaceutical compositions. Examples for pharmaceutically useful proteins or peptides are insulin, erythropoietin, BMPs, interferons, etc. Another example is a gastric juice protein with mucosal protective activity which was recently isolated and named BPC. WO 92/04368 relates to BPC which exhibits body-protective activity and has a molecular weight of about 40,000 daltons, its preparation and its use. WO 93/24521 and WO 94/11394 disclose BPC peptides which have organo-protective activity of the same type as known from the parent protein BPC. Sikiric et al. in: *Digestive Diseases and Sciences*, 41(1996)7, 1518–1526, describe pentadecapeptide BPC 157, which exhibits when dissolved in water and saline salutary and prophylactic effects on acute pancreatitis and concomitant gastroduodenal lesions in rats.

Thus, the BPC peptides are known for a wide variety of pharmaceutical applications. However, the physicochemical stability of these peptides, for instance in normal saline, is not satisfactory. Furthermore, the application of BPC peptides, in particular by injection of an aqueous solution or in normal saline, causes pain and/or necrosis.

Salts of proteins and peptides are well known in the art. It is for instance known from Bertrand, M. et al. in: *Journal of Peptide Research*, 49 (1997)3, 269–272, that the effects of particular salts are very selective in respect to the stability and structure of peptides. For instance, the addition of monovalent cations, such as $NH_4^+$ to a final 0.1 M peptide (poly (Glu-Leu)) solution, induces a transition to a water soluable beta-structure. In contrast, no transition was observed using $Li^+$, $Na^+$, or $Cs^+$ ions.

SUMMARY OF THE INVENTION

The role of surface-accessable ion pairs in protein stability was investigated by determining the effects of added salts ($KCl$, $MgCl_2$ and $LaCl$) at neutral and acidic pH upon the stability of de novo designed two-stranded alpha-helical coiled-coils. The results show that added salt may have complex effects on protein stability, involving stabilizing and destabilizing contributions, whereby the net effect depends upon the nature of the charged residues and ionic interactions present in the protein (Kohn et al. in: *Journal of Molecular Biology*, 267 (1997)4,1039–1052)

Previous studies of model peptides have also shown that salt bridges spaced at i,i +4 along the peptide chain are more stabilizing than those spaced at i,i +3, with a preference for the order acid-base rather than base-acid from the N- to the C- terminus. However, at present it is not known whether surface salt bridges have a strong stabilizing effect on the native structure in proteins (Berger et al. in: *Journal of Biomolecular Structure and Dynamics*, 14 (1996)3, 285–291).

Thus, the properties of peptide salts with respect to their stability, structure and function depend very much upon the specific ions involved in forming the specific salt and other intrinsic or extrinsic factors. At present, it cannot be foreseen which particular properties a specific salt of a specific peptide might have.

DESCRIPTION OF PREFERRED EMBODIMENT

The technical problem underlying the present invention is to provide BPC peptides in more stable form and a diagnostic and/or pharmaceutical composition comprising BPC peptides exhibiting improved stability and at least the same pharmaceutical activities as the BPC peptides themselves. Furthermore, the technical problem underlying the present invention is to provide a pharmaceutical composition which overcomes the drawbacks mentioned above, in particular, allowing painless injection of BPC peptides. The present invention solves these problems by providing BPC peptide salts and a pharmaceutical or diagnostic composition comprising a pharmaceutically or diagnostically effective amount of the salts of BPC peptides, wherein the anion of the salt is a negatively charged peptide comprising 8 to 15 amino acids, exhibiting a molecular weight of 900 to 1,600 daltons and having the general formula (I)

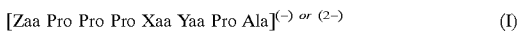

$$[\text{Zaa Pro Pro Pro Xaa Yaa Pro Ala}]^{(-) \text{ or } (2-)} \qquad (I)$$

wherein Xaa is a neutral aliphatic amino acid residue, in particular Ala, bAla, Leu, Ile, Gly, Val, Nle or Nva, Yaa is a basic amino acid residue, in particular Lys, Arg, Orn or His and Zaa is an acidic amino acid residue, in particular Glu, Asp, Aad or Apm and wherein the cation of the salt is the cation of an inorganic or organic nontoxic and pharmaceutically acceptable base. In particular, the cation of the salt is an alkali metal or an alkaline earth metal, for instance $Na^+$, $K^+$, $Li^+$, $Cs^+$, $Ca^+$, or another metal, such as $Zn^{2+}$, or a primary, secondary or tertiary amine or organic compound, such as $NH_4^+$, triethanolamine$^+$, cyclohexylamine$^+$, 2-AMP$^+$ (2-amino-1-propanol) or TRIS$^+$ (Tris-(hydroxymethyl)-aminomethan), as long as these cations are physiologically acceptable.

Surprisingly, the BPC peptide salts of the present invention show at least the same pharmaceutical activity as the BPC peptides and, additionally, a remarkably increased physicochemical stability in comparison with the free BPC peptides or acetates of BPC peptides. The cation used according to the present invention does not influence the activity of the BPC peptides, but increases their stability. The BPC peptide salts of the present invention are, for instance, more stable than BPC peptides or BPC peptide acetates in normal saline or water. Furthermore, the salts of the present invention are well suited for peroral use and do not exhibit any undesired side effects such as pain or necrosis during or after application, in particular, by injection. The BPC peptide salts of the present invention therefore allow an improved enteral and parenteral application. Furthermore, the salts of the present invention are very favorable due to the absence of any signs of toxicity up to doses of 50 mg/kg b.w., (body weight).

The salts of the invention can be obtained by dissolving the free BPC peptide in an aqueous or aqueous/alcoholic solvent or in other suitable solvents with an appropriate base and then isolating the obtained salt of the invention by evaporating the solution, by freezing and lyophilization or by addition of another solvent, e.g. diethylether, to the aqueous and/or alcoholic solution of the BPC peptide salt inducing the separation of unsoluble crude salt. For salt formation, usually one or maximal two mols of base, i.e. cation, and one mol of the free BPC peptide are used. For the preparation of alkali BPC peptide salts, alkali metal carbonates or hydrogencarbonates are preferably used. The prepared peptide salts are freely soluble in water. Thus, the present invention also relates to a process for the preparation of the BPC peptide salts.

In the context of the present invention, a base is considered as a substance capable of forming a cation in a solution, particularly in an aqueous and aqueous/alcoholic solution.

In the context of the present invention, pharmaceutical activity encompasses prophylactic and therapeutic activities. Accordingly, a pharmaceutical composition refers to compositions exhibiting prophylactic and/or therapeutic activities.

Additionally, the invention relates to a pharmaceutical or diagnostic composition comprising the BPC peptide salts of the present invention, optionally in conjunction with one or more pharmaceutically acceptable carriers, as well as processes for preparing these compositions. These compositions are suitable for topical or systemic application, for instance in the form of injectable solutions, tablets, creams, capsules, ointments, lotions, lingualeftes etc. The dosage is preferable in the range from $10^{-5}$ to $10^{-2}$ mg/kg of body weight, applied systemically or topically in higher concentration between 0.1% to 0.5%. The determination of the optimum dosages for a particular treatment is within the skill of the art.

The present invention also relates to a pharmaceutical or diagnostic composition according to the above, which in addition to one or more of the BPC peptide salts of the present invention, contains trehalose, in particular for peroral use, and/or pharmaceutically or diagnostically acceptable carriers, dilutents and/or additives.

The composition, preferably the water-soluble composition, of the invention may, in addition to the BPC peptide salt, further contain a water-soluble protein injectable into body fluids without showing any substantial pharmacological activity at the concentration used in one unit dosage form of the present invention (hereinafter, "water-soluble protein"). As such a water-soluble protein, serum albumin, globulin, collagen and/or gelatin are preferred. This protein can be added in an amount generally employed in injectable pharmaceutical compositions. Thus, for example, the weight ratio between the water-soluble protein and the BPC peptide salt is about 0.0001:1 to 100:1, preferably about 0.001:1 to about 10:1 or more preferably about 0.01:1 to about 1:1.

Continuing, the invention also relates to the aforementioned BPC peptide salts themselves and compositions containing them, in particular, in dried and/or pure form or in an aqueous or aqueous/alcoholic solution. The pH of a solution prepared from the water-soluble composition or a peptide salt of the present invention should be such that said pH will not exert any adverse influence upon the activity of the pharmacologically active peptide, but is within an acceptable range for injections in general and further, such that said pH will neither cause a great change in viscosity of the solution nor allow formation of a precipitate or the like. Thus the solution should preferably have a pH of about 6 to 9, preferably 6,5 to 7,5.

When the water-soluble composition of the invention is converted into an aqueous solution for administration, the concentration of the pharmacologically active peptide salt in said solution should preferably be about 0.0000001 to 10% (w/v), more preferably about 0.000001 to 5% (w/v) or most preferably about 0.00001 to 1% (w/v).

The composition of the present invention should preferably have a unit dosage form containing the pharmacologically active BPC peptide salt of the invention and, if necessary, together with further additives such as the above-mentioned water-soluble protein. Thus, for example, the two or three components mentioned above are made to occur in an ampule or vial by dissolving or suspending them in sterile water or sterile physiological saline. In this case, the method of preparation may comprise admixing a solution of the pharmacologically active BPC peptide salt and further, if necessary, a solution of the additive or adding the additive in a powder form to a solution of the pharmacologically active BPC peptide salt or any other combination of adequate procedures. The dosage form may also be prepared by adding sterile water or sterile physiological saline to a lyophilizate or vacuum-dried powder in which the pharmacologically active BPC peptide salt, and if necessary the additive, coexist. This unit dosage form may contain one or more conventional additives such as pH adjusting agents (e.g. glycine, hydrochloric acid, sodium hydroxide), local anesthetics (e.g. xylocaine hydrochloride, chlorobutanol), isotonizing agents (e.g. sodium chloride, mannitol, sorbitol), emulsifiers, adsorption inhibitors (e.g. Tween® 60 or 80), talcum, starch, lactose and tragacanth, magnesium stearate, glycerol, propylen glycol, preserving agents, benzyl alcohol, methylhydroxy benzoate and/or oleum arachid hydrogen. This unit dosage form may further contain pharmaceutically acceptable excipients such as polyethylene glycol 400 or dextran.

The water-soluble composition of the present invention preferably takes the form of a parenteral preparation. As said parenteral preparation, injectable solutions, solutions for transmucosal administration, nasal solutions, otic solutions are preferred.

Said injectable solutions include solutions for intravenous administration, subcutaneous administration, intraarterial administration, intramuscular administration and intraocular administration. These long-acting preparations can be readily drawn from ampules or vials into syringes. Bubbles, if formed upon drawing, can be readily eliminated by a short time of mere standing.

The composition of the present invention may be in a form dissolved in water or in a lyophilized form with a crystallizing solute such as mannitol. Addition of sterile water or sterile physiological saline to the lyophilizate gives an aqueous solution.

The tonicity of an aqueous solution of the water-soluble composition of the present invention should be within the tolerable range when administered and is adjusted, for example, by isotonizing agents such as sodium chloride and mannitol. The tonicity is preferably from half to twice as high as that of physiological saline, more preferably from three-quarters to one and a half as high as that of physiological saline.

The viscosity of an aqueous solution of the water-soluble composition of the present invention should be low enough to be injected. The viscosity is preferably lower than 500 cP, more preferably lower than 400 cP. The values of the viscosity corresponds to those measured by employing Cone LD in an E type viscosity meter (TOKIMEC, Japan) at 25° C.

When the composition is in the form of a lyophilizate, it is preferred that the viscosity, the tonicity of and the component concentrations in the aqueous solution derived therefrom is within the respective ranges mentioned hereinbefore.

The composition of the present invention is made by admixing these ingredients according to a conventional method. The goal of admixing the ingredients of the present composition should be such that the activity of the pharmacologically active BPC salt is maintained and bubble formation minimized during the process. The ingredients are put into a vessel (for example a bottle or drum) either at the same time or in any order. The atmosphere in the vessel can be, for example, sterile clean air or sterile clean nitrogen gas. The resultant solution can be transferred to small vials or ampules and can be further subjected to lyophilization.

The liquid form or the lyophilizate powder form of the composition of the present invention may be dissolved or dispersed in a solution of a biodegradable polymer such as poly(lactic-glycolic) acid copolymer, poly(hydroxybutyric acid), poly(hydroxybutyric-glycolic) acid copolymer, or the mixture of these, and then may be formulated, for example, to films, microcapsules (microspheres), or nanocapsules (nanospheres), particularly in the form of soft or hard capsules.

In addition, the composition of the present invention encapsulated in liposomes comprising phospholipids, cholesterol or the derivatives of these can be further dispersed in physiological saline or a hyaluronic acid solution dissolved in physiological saline.

The soft capsule may be filled with the liquid form of the composition of the present invention. The hard capsule may be filled with the lyophilizate powder of the composition of the present invention, or the lyophilizate powder of the present composition may be compressed to tablets for rectal administration or oral administration respectively.

Of course, the composition of the present invention can be supplied in a pre-filled syringe for self-administration.

The composition of the present invention may be maintained at normal temperature such as from +10° C. to +30° C. or at normal refrigeration range, preferably from about +2° C. to +8° C.

The invention also relates to novel uses and methods of treatments using the aforementioned salts and/or compositions, in particular, with respect to the treatment of disturbances connected with either nitric oxide (NO) formation or impaired NO-system functions, in particular, hypertension, angina, impotence, circulatory and septic shock, stroke, inflammation, respiratory distress syndrome, adhesion and aggregation of platelets and leukocytes, endothelial dysfunction, gastrointestinal lesions, peristalsis disturbances, diabetes, pancreatitis, hypotension and Parkinson's disease; dysfunctions or hyperfunctions of somatosensory nerves, in particular sensory neuropathy, postherpetic neuralgia, atopic dermatitis, impaired healing of injured tissue, acquired cold and heat urticaria, psoriasis, bullous pemphigoid, eczema, photodermatoses, chronic arthritis, gastrointestinal lesions and specific or non-specific hyperreactivity of upper and lower respiratory tracts (asthma, rhinitis); endothelium disturbances; wounds, ulcers; conditions relating to acute and/or chronic inflammation, in particular, chronic arthritis, and disorders related with delayed type of hypersensitivity, and gastrointestinal lesions; liver disorders, organ lesions induced by free radicals specifically caused by irradiation; disorders connected with cathecholaminergic system disturbances, in particular, schizophrenia, amphetamine challenge effects, drug abuse; stress related conditions; acute pancreatitis, with an additional positive impact on concomitant gastroduodenal pathology; cardiac disturbances, in particular, antiarrhythmic, antianginal and cardioprotective treatment; depressive disturbances; Parkinson's disease and Parkinson's disease-like pathology; temperature disturbances; bone impairments; hypertension-induced various organ damages; disturbances of coagulation; pain disturbances; convulsion disorders; spinal cord injury; alcohol injuries, induced by alcohol abuse or increased alcohol intake; brain ischemic disorders; peripheral nerve injuries; cataleptic disorders and neuroleptic disturbances; disorders related to abnormal or mutant lymphocytes; disturbances of fetuses; vaginal atrophy and osteoporosis development caused by ovariectomy conditions; tumors; viral diseases, in particular AIDS or ARC; gastrointestinal lesions; cognitive disorders; withdrawal disturbances; kidney disturbances and disturbances in cellular immune response.

The present invention furthermore relates to a BPC peptide salt or a pharmaceutical or diagnostic composition according to the above wherein the general formula (II) is Xaa Zaa Pro Pro Pro Xaa Yaa Pro Ala Asp Zaa Ala Xaa Xaa Xaa (SEQ ID No. 2).

The present invention relates in particular to a BPC peptide salt or a pharmaceutical or diagnostic composition comprising a salt of a BPC peptide according to the above general formula (I) wherein the peptide is selected from the group consisting of:

Leu Glu Pro Pro Pro Gly Lys Pro Ala Asp Asp Ala Leu Gly Val (SEQ ID No. 3);

Gly Glu Pro Pro Pro Gly Lys Pro Ala Asp Asp Ala Gly Leu Val (SEQ ID No. 4)

(also called BPC157);

Leu Glu Pro Pro Pro Leu Lys Pro Ala Asp Asp Ala Leu Gly Val (SEQ ID No. 5);

Leu Glu Pro Pro Pro Leu Lys Pro Ala Asp Ala Leu Gly Val (SEQ ID No. 6);

Gly Glu Pro Pro Pro Gly Lys Pro Ala Asp Ala Gly Leu Val (SEQ ID No. 7);

Glu Pro Pro Pro Leu Lys Pro Ala (SEQ ID No. 8);

Asp Pro Pro Pro lee Arg Pro Ala Asp (SEQ ID No. 9);

Glu Pro Pro Pro Leu Lys Pro Ala Asp (SEQ ID No. 10);

Leu Glu Pro Pro Pro Leu Lys Pro Ala Asp Ala Leu Gly Val (SEQ ID No. 11);

Gly Glu Pro Pro Pro Gly Arg Pro Ala Asp (SEQ ID No. 12) and

Glu Pro Pro Pro Leu Lys Pro Ala Asn (SEQ ID No. 13).

These peptides are known from WO 94/11394 and WO 93/24521, whose contents are incorporated in the present disclosure with respect to the preparation and use of the BPC peptides.

Furthermore, the peptides may be linked to other functional and/or structural moieties such as carbohydrates, fats, proteins or peptides, antibodies, receptors, hormones, cytotoxic substances, marker substances, dyes, radioactive labels, immunomodulatory agents, drugs, carriers, targeting or signalling substances, etc.

Additionally, the invention relates to the abovementioned BPC peptide salts and compositions wherein the peptide is in linear or cyclized form, in particular, cyclized by an amide bond between the first and the last amino acid residue.

The invention will now be explained in more detail by way of illustrative examples and the accompanying figures. The figures show:

EXAMPLE 1

Preparation of the Monosodium Salt of BPC157 (NaBPC157)

0.5 g (0.35 mmol) of a pentadecapeptide with the sequence Gly Glu Pro Pro Pro Gly Lys Pro Ala Asp Asp Ala Gly Leu Val (BPC157) was dissolved in 10 ml water containing 29.6 mg of sodium hydrogencarbonate (0.35 mmol), sterile filtered through a 0.2$\mu$ filter and dried by freeze-drying to give 0.48 g of an off-white solid.

Purity of the obtained salt: 99.4% (HPLC). Mass spectrum (FAB): 1419, higher ions at 1441 (M$^+$Na$^+$).

The amino acid analysis of the obtained peptide salt after 72 hours of hydrolysis with 6N—HCl in a sealed tube at 110° C. gave values corresponding to the composition: 3Gly, 4Pro, 2Ala, 2Asp, Glu, Leu, Val, Lys.

Figure 1:
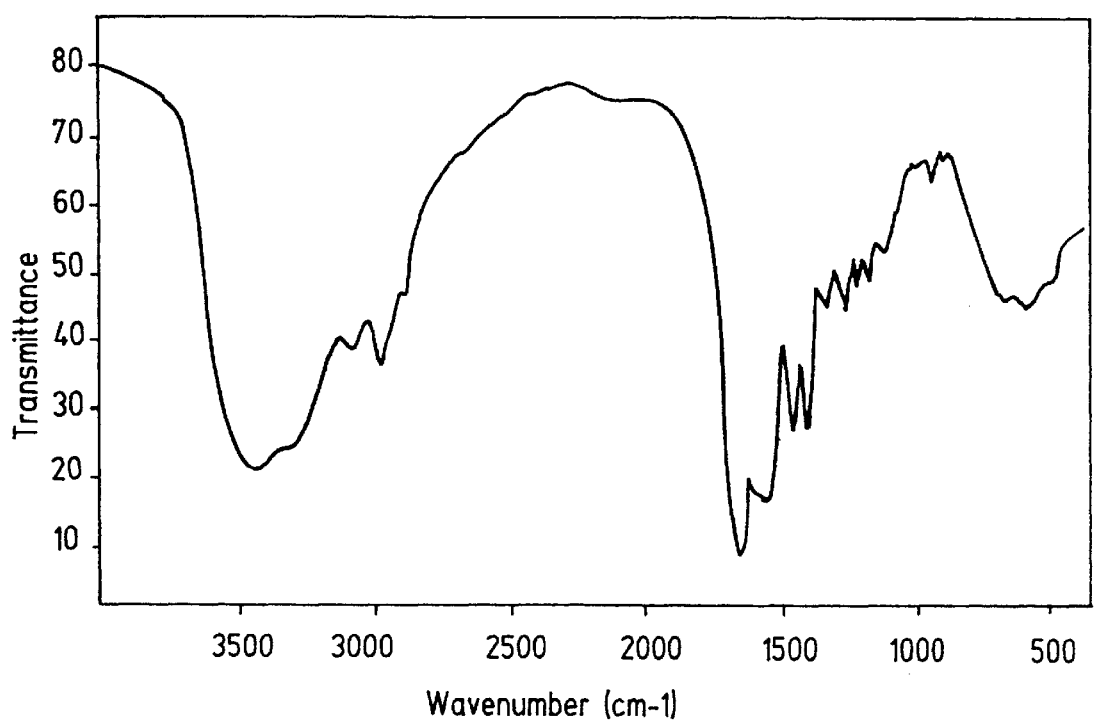
FIG. 1 shows the IR spectrum of NaBPC157.

IR spectrum (KBr): FIG. 1. UV spectrum (H$_2$O): $\lambda$max=190 nm, no other maxima. Melting point: 288–290° C. (decomposition).

EXAMPLE 2

Preparation of the Disodium Salt of BPC157 (Na$_2$BPC157)

0.5 g (0.35 mmol) BPC157 was dissolved in 10 ml of ethanol. 1.4 ml of 0.5 mol/L of methanolic sodium hydroxide was added whilst stirring moderately. This solution was sterile filtered through a 0.2$\mu$ filter and slowly added to a stirred diethylether (50 ml). The separated white solid was filtered and washed with diethylether to give 0.52 g of the disodium salt.

Purity of the obtained salt: 99.4% (HPLC). Mass spectrum (FAB): 1419, higher ions at 1441 (M$^+$Na$^+$), 1464 (M$^+$Na$_2$$^+$).

The amino acid analysis of the obtained peptide salt corresponds to the composition: 3Gly, 4Pro, 2Ala, 2Asp, Glu, Leu, Val, Lys.

Figure 2:
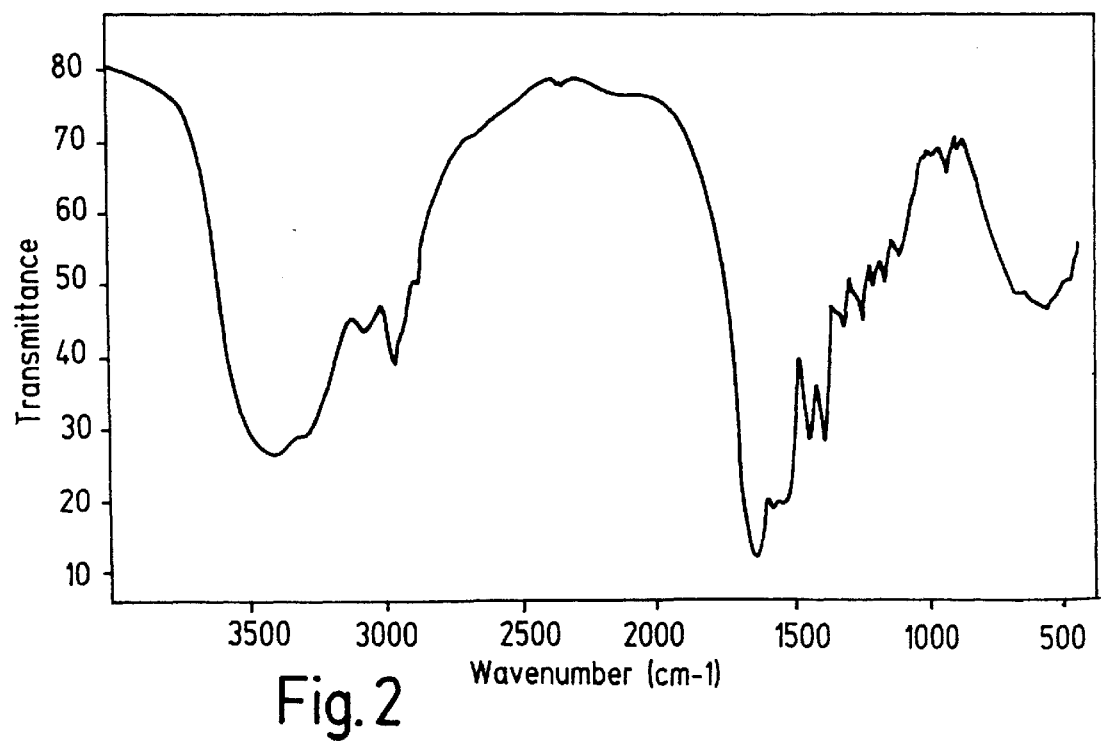
FIG. 2 shows the IR spectrum of Na$_2$BPC157.

IR spectrum (KBr): FIG. 2. UV spectrum (H$_2$O): $\lambda$max=190 nm, no other maxima. Melting point: 275–277° C.

EXAMPLE 3

Preparation of the Dicesium Salt of BPC157 (Cs$_2$BPC157)

0.5 g (0.35 mmol) BPC157 was dissolved in 8 ml of water containing 114 mg cesium carbonate (0.70 mmol), sterile filtered through a 0.2$\mu$ filter and lyophilized to give 0.55 g of an off-white solid.

Purity of the obtained salt: 99.3% (HPLC). Mass spectrum (FAB): 1419, higher ions at 1551 (M$^+$Cs$^+$), 1684 (M$^+$Cs$_2$$^+$).

The amino acid analysis of the obtained peptide salt corresponds to the composition: 3Gly, 4Pro, 2Ala, 2Asp, Glu, Leu, Val, Lys.

Figure 3:
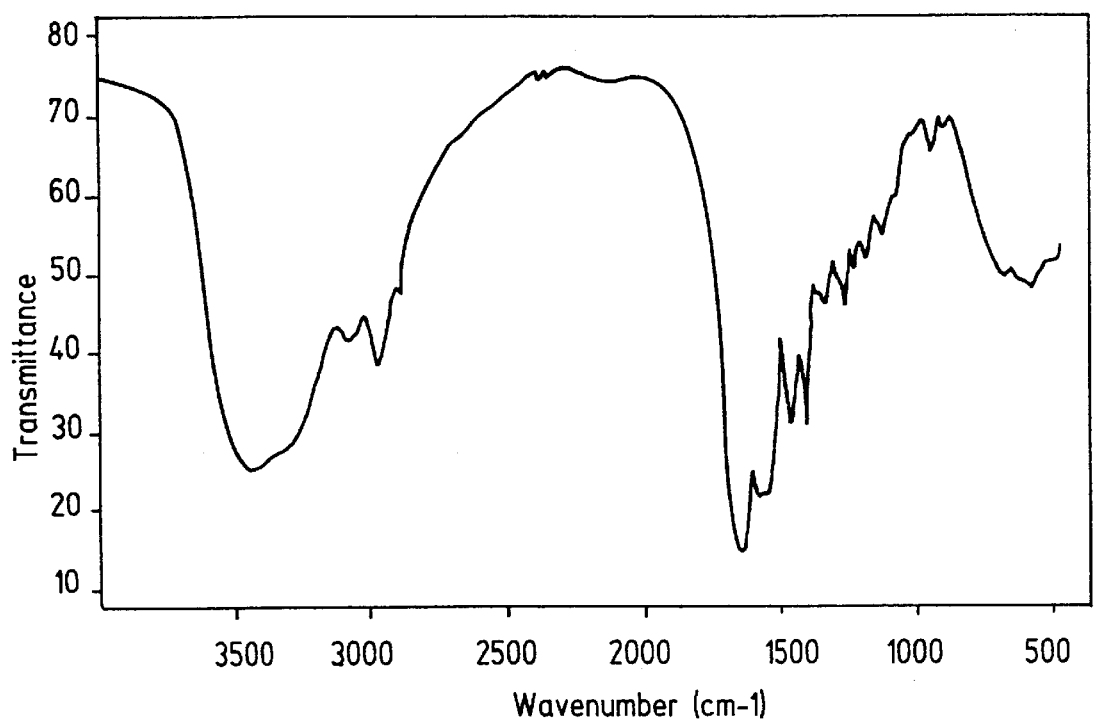
FIG. 3 shows the IR spectrum of the dicesium salt of BPC157 (Cs$_2$BPC157).

IR spectrum (KBr): FIG. 3. UV spectrum (H$_2$O): $\lambda$max=190 nm. Melting point: 268° C.

EXAMPLE 4

Preparation of the TRIS Salt of BPC157 (TRIS-BPC157)

0.5 g (0.35 mmol) BPC157 was dissolved in 10 ml of methanol containing 42.6 mg (0.35 mmol) of tris-(hydroxymethyl)-aminomethane (TRIS), sterile filtered through a 0.2$\mu$ filter and dried by evaporation of methanol in a vacuum at 40° C. to obtain 0.56 g of white solid.

Figure 4:
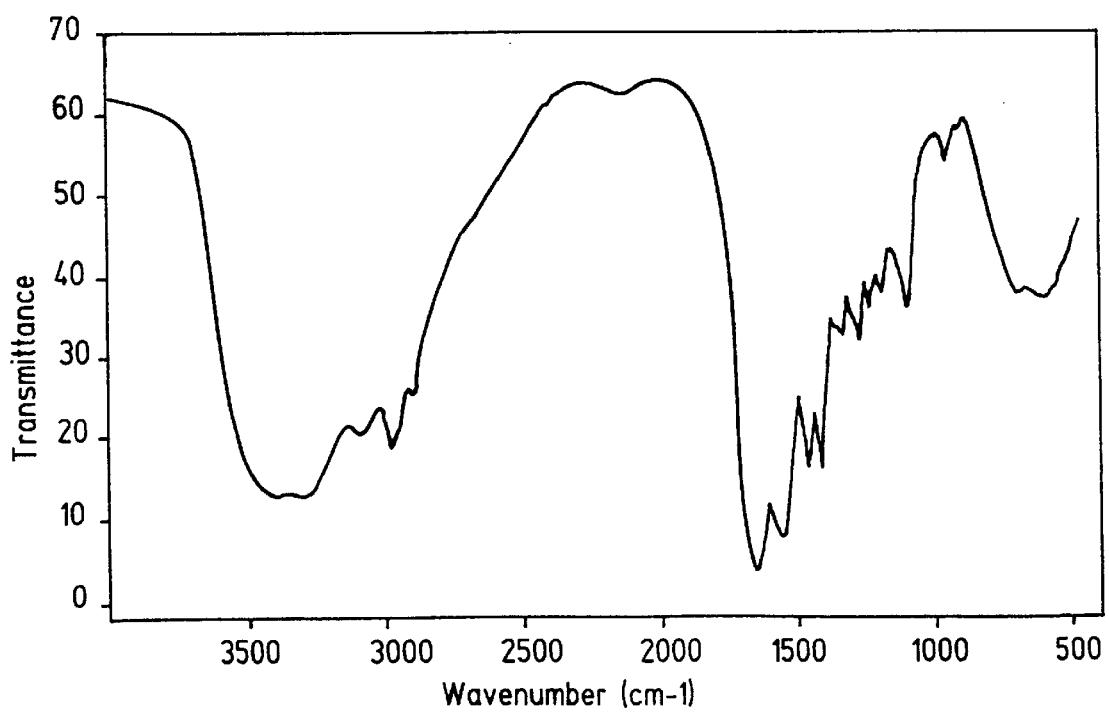
FIG. 4 shows the IR spectrum of the TRIS salt of BPC157 (TRIS-BPC157).

Purity of the obtained salt: 99.5% (HPLC) Mass Spectrum (FAB): 1419 (MH$^+$). The amino acid analysis of the obtained peptide salt corresponds to the composition: 3Gly, 4Pro, 2Ala, 2Asp, Glu, Leu, Val, Lys. IR spectrum (KBr): FIG. 4. UV spectrum (H$_2$O): $\lambda$max=190 nm. Melting point: 250° C. (decomposition).

EXAMPLE 5

Preparation of the di-TRIS Salt of BPC157 ((TRIS)$_2$BPC157)

The compound was prepared according to the procedure described in Example 1, with the exception that 85.2 mg (0.70 mmol) TRIS was used.

Figure 5:
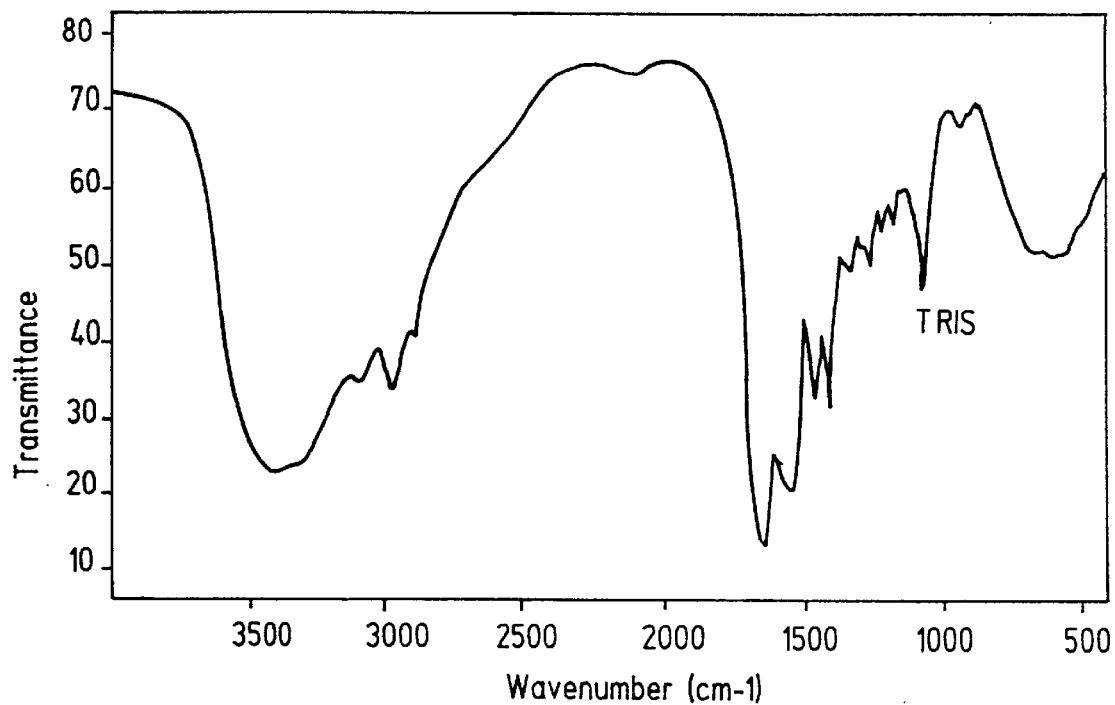
FIG. 5 shows the IR spectrum of the di-TRIS salt of BPC157 ((TRIS)$_2$BPC157).

Purity of the obtained salt: 99.5% (HPLC). Mass Spectrum (FAB): 1419 (MH$^+$). The amino acid analysis of the obtained peptide salt corresponds to the composition: 3Gly, 4Pro, 2Ala, 2Asp, Glu, Leu, Val, Lys. IR spectrum (KBr): FIG. 5. UV spectrum (H$_2$O): $\lambda$max=190 nm. Melting point: 188°–193° C.

EXAMPLE 6

Preparation of the 2-aminopropanol Salt of BPC157 (2-AMP-BPC157)

The compound was prepared according to the procedure described in Example 1. 2-aminopropanol (2-AMP) was used as a base.

Figure 6:
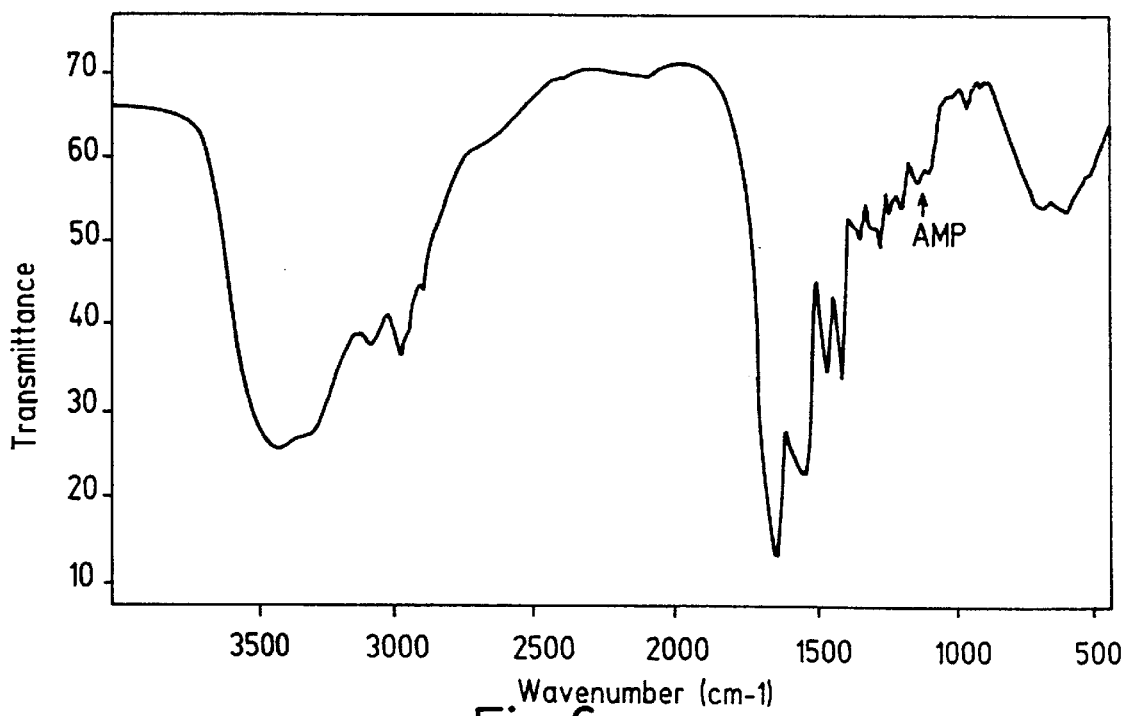
FIG. 6 shows the IR spectrum of the 2-aminopropanol salt of BPC157 (2-AMP-BPC157).

Purity of the obtained salt: 96.6% (HPLC). Mass spectrum (FAB): 1419 (MH$^+$). The amino acid analysis of the obtained peptide salt corresponds to the composition: 3Gly, 4Pro, 2Ala, 2Asp, Glu, Leu, Val, Lys. IR spectrum (KBr): FIG. 6. UV spectrum (H$_2$O): $\lambda$max=190 nm. Melting point: 158° C. (decomposition.).

EXAMPLE 7

Preparation of the Triethanolamine Salt of BPC157 (TEAM-BPC157)

The compound was prepared according to the procedure described in Example 1. Triethanolamine (TEAM) was used as a base.

Figure 7:
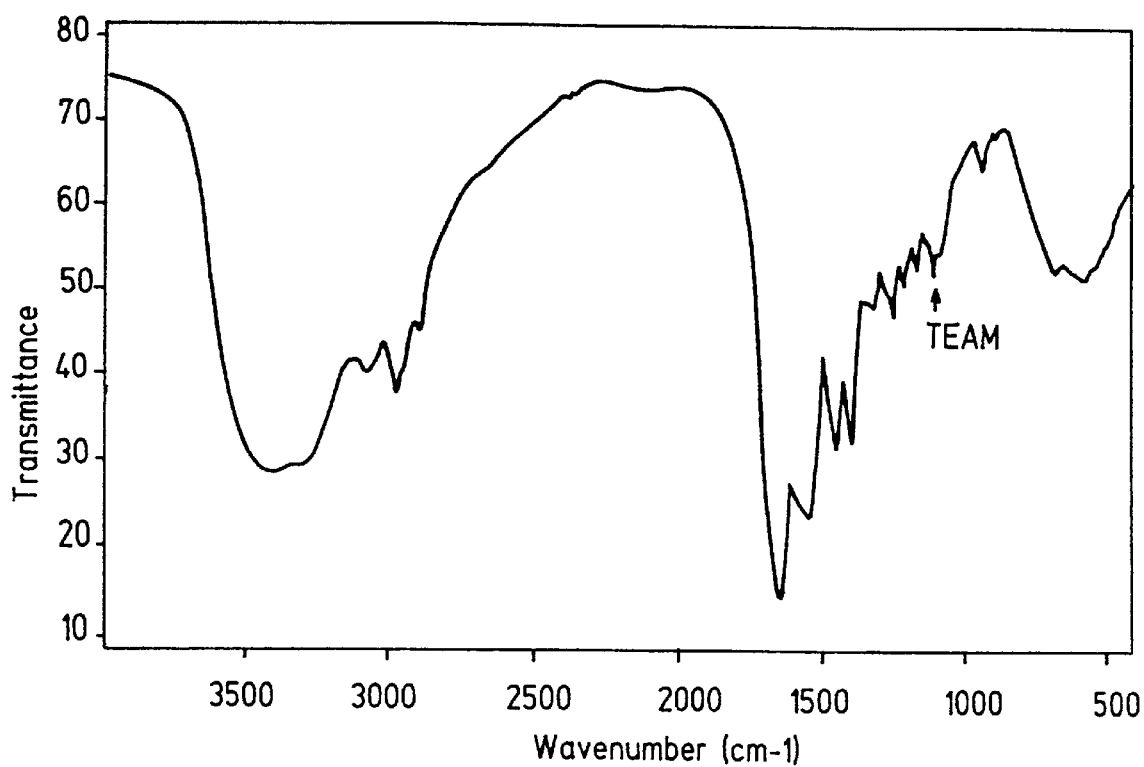
FIG. 7 shows the IR spectrum of the triethanolamine salt of BPC157 (TEAM-BPC157).

Purity of the obtained salt: 99.2% (HPLC). Mass Spectrum (FAB): 1419 (MH$^+$). The amino acid analysis of the obtained peptide salt corresponds to the composition: 3 Gly, 4 Pro, 2 Ala, 2Asp, Glu, Leu, Val, Lys. IR spectrum (KBr): FIG. 7. UV spectrum (H$_2$O): $\lambda$max=190 nm. Melting point: 202°–205° C.

EXAMPLE 8

Preparation of Tablets Containing TRIS-BPC157

| Composition | mg/tablet |
|---|---|
| TRIS-BPG157 | 0.5 |
| trehalose | 20.0 |
| lactose | 17.0 |
| starch | 6.5 |
| talcum | 3.0 |
| tragacanth | 2.5 |
| magnesium stearate | 0.5 |
| | 50.0 mg |

TRIS-BPC157 (0.5 mg) and trehalose (20 mg) were dissolved in 1 ml of water and dried by evaporation. After drying, the crude residue was admixed with the other ingredients to prepare the tablets.

EXAMPLE 9

Preparation of Capsules Containing NaBPC157

| Composition | mg/capsule |
|---|---|
| NaBPC157 | 0.5 |
| trehalose | 60.0 |
| lactose | 39.0 |
| magnesium stearate | 0.5 |
| | 100.0 mg |

NaBPC157 (0.5 mg) and trehalose (60 mg) were dissolved in 1 ml of water and dried by evaporation of the solvent. The crude residue was admixed with the other ingredients to prepare the capsules.

EXAMPLE 10

Preparation of a Solution Containing NaBPC157

| Composition | g/25 ml |
|---|---|
| NaBPC157 | 0.05 |
| glycerol | 15.00 |
| benzyl alcohol | 0.01 |
| buffer pH 7.0 added to | 25 ml |

EXAMPLE 11

Preparation of a Cream Containing TRIS-BPC157

| Composition | g/25 g |
|---|---|
| TRIS-BPC157 | 0.05 |
| emulsifier | 2.80 |
| oleum arachid hydrogen | 7.08 |
| Tween ® 60 | 12.08 |
| propylen glycol | 3.00 |
| methylhydroxy benzoate | 0.07 |
| | 25.00 g |

EXAMPLE 12

Stability Tests

The stability of the BPC peptide salts was tested by incubation of the salts for 76 and 120 days at 40° C. The concentration of the BPC peptides salts in an aqueous solution was 0.2% (w/v). The stability was measured using the HPLC method: column Kromasil 100, 5$\mu$, 150×4.6 mm, mobile phase 0.1% triflouroacetic acid in water/acetonitrile (from 0 to 50 vol. %), gradient elution in 25 minutes, flow 1 ml/min, detection: UV at 214 nm.

For comparison, the free BPC peptide and its monoacetate were used.

TABLE 1

The stability of the BPC peptide salts at 40° C. on days 0, 76 and 120; assay in area % (HPLC).

| Compound | pH-value; 0.2% in water | 0 Days | 76 Days | 120 Days |
|---|---|---|---|---|
| free peptide BPC157 | 4.46 | 99.3 | 98.1 | 97.4 |
| peptide BPC157 monoacetate | 4.53 | 99.2 | 97.8 | 95.3 |
| sodium salt of BPC157 | 6.51 | 99.4 | 99.5 | 99.4 |
| disodium salt of BPC157 | 7.64 | 99.4 | 99.7 | 99.4 |
| TRIS salt of BPC157 | 6.31 | 99.5 | 99.5 | 99.4 |
| diTRIS salt of BPC157 | 8.24 | 99.5 | 99.5 | 99.5 |
| 2-AMP salt of BPC157 | 8.20 | 99.6 | 99.4 | 99.5 |
| TEAM salt of BPC157 | 7.61 | 99.2 | 99.3 | 99.1 |

The data presented in this table clearly demonstrate the increased stability of the BPC peptide salts of the present invention in contrast to free BPC peptide or its monoacetate. Furthermore, probably due to the high pH value of the BPC peptide salt solution, the injection of these solutions does not cause any pain or necrosis.

In another separate experiment, an additional improvement of the stability of the BPC peptide salts of the present invention in crude form and in solutions was observed after the addition of trehalose. Therefore, the addition of trehalose as a pharmaceutically acceptable additive for the preparation of a pharmaceutical composition, in particular, in the form of tablets or capsules, is another important aspect of the present invention.

The following examples describe experiments demonstrating the pharmaceutical activities of the BPC peptide salts of the present invention. These experiments have been done using different common models "in vitro" and "in vivo". For the experiments, the monosodium salt of BPC peptide 157 was used (abbrev.: NaBPC157), unless otherwise specified. Male Wistar rats, 250–280 g body weight, were used in all experiments, unless otherwise specified.

EXAMPLE 13

NO-System

Introduction:

Nitric oxide (NO) functions both as a signaling molecule in endothelial and nerve cells and as a killer molecule activated by immune cells. Recent investigations demonstrate that it can be used as a medicine by inhalation. In general, by either excess or impairment, NO appears to cause or contribute to a variety of disturbances, in particular, hypertension, angina, impotence, circulatory shock, septic shock, stroke, inflammation, respiratory distress syndromes, pulmonary hypertension, adhesion and aggregation of platelets and leukocytes, diabetes, hypotension, and Parkinson's disease.

Materials and Methods:

Some of the effects of NaBPC157 (10 μg or 10 ng/kg) were challenged in rats, such as the salutary activity against gastric lesions and NaBPC157's activity with respect to blood pressure maintenance. The lesions were obtained by using a 1 hour ethanol treatment (96%, i.e. (intragastrically)). NaBPC157 was simultaneously applied (i.p. (intraperitoneally)). In the blood pressure maintenance experiment, NaBPC157 was given intravenously (i.v.).

Also studied was the combined application of $N^G$-nitro-L-arginine methylester (L-NAME) (5 mg/kg i.v.), a competitive inhibitor of endothelium nitric oxide (NO)-generation and the NO-precursor L-arginine (200 mg/kg i.v.) (D-arginine was ineffective). In the gastric lesion assays, the NO-agents were given 5 minutes before the ethanol injury and the treatment with NaBPC157.

Results:

In the ethanol model, NaBPC157 given alone has an antiulcer effect as does L-arginine. NaBPC157 prevented the otherwise severe gastric lesions observed in ethanol treated control rats. L-NAME had no effect. L-NAME completely abolished the activity of L-arginine, but only attenuated the activity of NaBPC157. After application of a combination of L-NAME+L-arginine, the activity of NaBPC157 was additionally impaired.

In blood pressure studies, NaBPC157 (without effect on basal normal values) compared with L-arginine has both a mimicking effect (impaired L-NAME-blood pressure increase, applied prophylactically and decreased already raised L-NAME values, given at the time of the maximal L-NAME-blood pressure increase (i.e., 10 minutes after L-NAME)) and a preventative activity (L-arginine-induced moderate blood pressure decrease was prevented by NaBPC157 pre-treatment). When NaBPC157 was given 10 minutes after the application of the combination of L-NAME+L-arginine (still led to a blood pressure increase), its clear effect (noted in L-NAME treated rats) disappeared. In vitro, in gastric mucosa from stomach rat tissue homogenates, NaBPC157 given in the same dose (100 μM) as L-arginine, induced a comparable formation of NO. But NaBPC157's effect could not be inhibited by L-NAME, even with a tenfold (100 vs. 1000 μM) higher dose than needed for an inhibition of L-arginine's effect. On the other hand, NO-synthesis was lessened when NaBPC157 and L-arginine were combined. In summary, NaBPC157 could interfere with the NO-effects in both gastric mucosal integrity and blood pressure maintenance in a particular way, especially when combined with L-arginine, having a more prominent and/or particularly different effect on NO.

By having a more prominent effect on NO than does L-arginine, NaBPC157 could prevent the excessive NO formation associated side effects (the disturbed effect of L-arginine (e.g. hypotension)). These side effects were reversed toward normal values in vivo and excessive NO-formation was prevented in vitro. Additionally, the negative consequences of the NO-system inhibition (e.g. prevention of L-NAME induced blood pressure increase and reversal of the already established L-NAME-hypertension) were abolished.

Based on the close similarity of the NO-assays in other tissues (e.g. lung, liver, blood vessels, etc.) and the diversity of the applied models (gastric lesions and blood pressure maintenance), the noted beneficial effects of NaBPC157 with respect to both excessive NO-formation and impaired NO-system functions is evident. In particular, the BPC peptide salts of the present invention are useful for the treatment of hypertension, angina, impotence, circulatory shock, septic shock, stroke, inflammation, respiratory distress syndromes, pulmonary hypertension, pancreatitis, adhesion and aggregation of platelets and leukocytes, endothelial dysfunction, and Parkinson's disease.

EXAMPLE 14

Somatosensory Neurons

Introduction:

Somatosensory neurons are generally involved in the control of the homeostasis, particularly in the reaction to the challenges of homeostasis. These neurons can detect a potential threat. The neurons are, per se, able to immediately initiate appropriate measures to alleviate the danger. Vasoactive afferent neurons thus represent a system of first line defence against trauma. In general, their protective ability was evidenced by the experimental damage of the skin and gastrointestinal mucosa. Either dysfunctions or hyperfunctions are implicated in a variety of disorders, particularly congenital sensory neuropathy, sensory neuropathy caused by diabetes, herpes zoster, postherpetic neuralgia, atopic dermatitis, impaired healing of injured tissue (e.g. persistent skin wounds, aggravation of acid-induced skin lesions and formation of keratitis-like lesions in the cornea), acquired cold and heat urticaria, psoriasis, bullous pemphigoid, eczema, photodermatoses, upper and lower airway disorders, specific and non-specific hyperreactivity, vasomotor rhinitis, asthma, chronic arthritis, and gastrointestinal lesions.

Materials and Methods:

The gastroprotective effects of NaBPC157 on gastric lesions (produced in rats by treatment with 96% ethanol, restraint stress and indomethacin treatment) were studied. The possible involvement of sensory neurons in the salutary effects of NaBPC157 (10 μg/kg, 10 ng/kg i.p.) was studied with capsaicin which has quite distinct effects on sensory neurons: high dose administration to adult animals (125 mg/kg s.c., (subcutaneously) three months of age) or administration (50 mg/kg s.c.) to neonatal animals (seven days of age) destroys sensory fibers, whereas a low dose (500 μg/kg i.p.) activates a neurotransmitter release and protective effects on the mucosa.

Results:

(i) In the absence of capsaicin, NaBPC157 protected the gastric mucosa against ethanol, restraint stress and indomethacin application.

(ii) In the presence of neurotoxic doses of capsaicin, the negative influence of capsaicin on restraint stress, ethanol or indomethacin lesions consistently affected the salutary activity of NaBPC157. NaBPC157's protection was still evident in the capsaicin treated models (either treated as adults or as neonatals) in all of these assays. After the neonatal capsaicin treatment, a complete abolition of the gastroprotection caused by NaBPC157 was noted if NaBPC157 was applied as a single ng-regimen. The mucosal protection was fully reversed when the same dose was used daily.

(iii) In conjunction with the excitatory dose of capsaicin, the beneficial activity of NaBPC157 is additionally increased.

Taken together, these data demonstrate complex synergistic interaction between the beneficial activity of NaBPC157 and peptidergic sensory afferent neuron activity. Considering the close similarity of the capsaicin effects in animals and humans and the above described experiment, NaBPC157 can be used for the treatment of the disturbances mentioned above.

EXAMPLE 15

Endothelium Protection

Introduction:

Vascular endothelium injuries are known to precede the development of and to be an essential prerequisite for gross organ injuries. Endothelium protection could reduce the damaging consequence of ishemia for mucosal integrity. As a useful model, the application of Monastral Blue in rats shortly before the application of a necrotizing agent (e.g. intragastrically applied ethanol) known to produce large lesions is widely accepted.

Materials and Methods:

All rats received i.v. Monastral Blue (MB) (Sigma Company, USA) (1.0 ml/kg b.w.) 3 minutes before ethanol treatment. The rats were sacrificed 1 minute after the ethanol treatment. NaBPC157 (10.0 µg/kg i.p.) or saline (5.0 ml/kg i.p.) was given 1 hour before the treatment of ethanol. Immediately after the sacrifice, the stomach was removed and the lesions were assessed by unbiased observers. Representative sections of the stomach and duodenum were processed for further histologic analysis.

The vascular injury was assessed in an early period (1 minute after ethanol treatment) using the Monastral Blue (MB) technique. The areal density of the stained mucosa was examined by TEM.

Results:

A strong reduction of the MB-staining was consistently noted in groups treated with NaBPC157. The close similarity of the used models with human conditions demonstrates the use of NaBPC157 for the treatment of conditions related with endothelium disturbances in human therapy.

EXAMPLE 16

Angiogenesis

Introduction:

Angiogenesis is of crucial importance for the generation of granulation tissue and wound and/or ulcer healing. Using a generally known method, angiogenic properties were studied.

Materials and Methods:

In each rat, two sterile sponges (1 cm×1 cm×0.25 cm (V=0.25 ml)) with the same quantities of NaBPC157, (solution 50 µg, 10 µg, 10 ng/ml) or the reference agents, cimetidine (10 mg, 100 mg, 500 mg/ml), ranitidine (2.5 mg, 25 mg, 250 mg/ml), famotidine (10 mg, 50 mg, 100 mg/ml) and sucralfate (1 mg, 5 mg, 10 mg/ml) were implanted subcutaneously in the lumbar region. The sponges were removed after three and seven days. They were then fixed in formalin and processed for histologic and histochemical evaluation and morphometry. The microscope used was: Leitz, DIAPLAN: For morphometric analysis, the program "SFORM" made by VAMS, Zagreb, Croatia was used.

Results:

Newly formed granulation tissue around the implanted sponge is used regularly as a valuable quantitative measure for host reaction on a foreign body. The experiments with rats sacrificed three days after implantation showed the following: in the groups of animals treated with NaBPC157, significantly more granulation tissue was noted compared with that of the control values. Similar results were observed in the rats treated with sucralfate in all of the dosages used. Contrary to this, no difference between the control values and the analyzed agent was observed in groups treated with all three H2-blockers. In the animals sacrificed seven days after implantation, those treated with all three doses of sucralfate and those treated with the highest dose of NaBPC157 (50 µg) were significantly different in comparison with the control group. The control values did not differ significantly between the two terms of sacrifice.

Inside the newly formed granulation tissue, the endothelial spaces were counted. Relative to the control values (the number of newly formed endothelial spaces in the control group three days after implantation was 7.94±1.23 and seven days after implantation 14.8±3.12), all used substances led to significantly increased values in both intervals (the third and seventh day).

In addition to the evidence that various antiulcer drugs share angiogenic properties, NaBPC157 also stimulates granulation formation, as does sucralfate. Accordingly, NaBPC157 can be used to initiate and support healing processes, in particular wound and/or ulcer healing processes.

EXAMPLE 17

Inflammation

Introduction:

Presently used anti-inflammatory agents are usually evaluated in many suitable models closely representing the acute and/or chronic inflammation disturbances in humans. However, severe gastrointestinal lesions appear as a major side effect of these agents.

An acute anti-inflammatory and analgetic activity was noted for NaBPC157 (e.g. turpentine, carrageenin, acetic acid or $MgSO_4$ writhing (prostaglandin-dependent, prostaglandin-non dependent) tail-pinching tests) along with an antipyretic effect (a decrease of yeast induced fever (4000 mg/kg s.c.)). Consequently, its known salutary effect on gastrointestinal lesions, its effect on chronic inflammation lesions such as adjuvant arthritis and its effect as a non-steroidal anti-inflammatory agent in NSAIAs-induced gastrointestinal lesions were simultaneously studied in rats.

Materials and Methods:

In gastrointestinal lesions (indomethacin (30 mg/kg s.c.), aspirin (400 mg/kg i.g.) and diclofenac (125 mg/kg i.p.)) studies, NaBPC157 (10 µg or 10 ng/kg i.p.) was given regularly, either simultaneously and/or one hour prior to drug application (indomethacin). In the adjuvant arthritis (tail-application of 0.2 ml of Freund's adjuvant) studies (14 days, 30 days, one year), NaBPC157 (10 µg or 10 ng/kg i.p.) was given as a single application (at 1 hour either before or following the application of Freund's adjuvant) or in a once-daily regimen (0–14$^{th}$ day, 14–30$^{th}$day and 14$^{th}$day-one year).

Results:

Given together with the investigated NSAIAs, NaBPC157 consistently reduced the otherwise prominent lesions in the stomach of the control rats, as well as the lesions in the small intestine in the indomethacin groups. In the adjuvant arthritis studies, the lesions' development was considerably reduced after a single NaBPC157 application and even more attenuated in rats treated daily with NaBPC157. As a therapy of already established adjuvant arthritis, the salutary effect of NaBPC157 consistently appeared after only two weeks of medication and it was clearly evident after one year of application. These data demonstrate the anti-inflammatory and protective effects of NaBPC157 on mucosal integrity.

Two distinct mechanisms, inflammation and delayed hypersensitivity, are known to be involved in the mediation of adjuvant arthritis. NaBPC157 positively effects both of them. Relative to reference standards (i.e., aspirin, indomethacin), NaBPC157 was effective in considerably lower doses ($\mu$g and ng/kg vs. mg/kg). This initial effectiveness in adjuvant arthritis prevention is even more enhanced in a daily application. Higher (10 $\mu$g/kg) dosage was effective either after a single or daily regimen, whereas lower (10 ng/kg) dosage, previously ineffective given as a single application, becomes efficacious when applied as a daily regimen. This finding, in conjunction with the therapeutic effect of NaBPC157 on fully established arthritis, evidences a useful application during the entire course of adjuvant arthritis. The noted effectiveness of NaBPC157 in adjuvant arthritis (prophylactic/therapeutic effect, non-established/established adjuvant arthritis) could not be observed with the presently used therapeutic agents. Glucocorticoids are effective in adjuvant arthritis prevention when applied daily, but not in short treatment. Immunosuppressants (in high dosage) and non-steroidal analgetics are effective only in pre-treatment or post-treatment respectively.

Thus, based on the close similarity between the used model and corresponding human disturbances, it is evident that NaBPC157 with its mucosal protective properties can be used for the treatment of conditions related to acute inflammation and chronic arthritis. Additionally, NaBPC157 can be used for the treatment of disorders related to the delayed type of hypersensitivity disturbances and gastrointestinal lesions induced in various parts of the gastrointestinal tract, particularly those induced by agents such as NSAIAs.

EXAMPLE 18

Free Radical Scavenger Effect
Materials and Methods:

The hepatoprotective effects of NaBPC157 were evaluated in comparison with reference standards such as bromocriptine, amantadine and somatostatin in various experimental models of liver injury in rats: 24 hour-bile duct and hepatic artery ligation, 48 hour-restraint stress and $CCl_4$ (a free radicals inducing agent) administration. NaBPC157 was administered either intragastrically or intraperitoneally.
Results:

NaBPC157 significantly prevented the development of liver necrosis or fatty changes in rats subjected to 24 hour bile duct and hepatic artery ligation, 48 hour restraint stress, and $CCl_4$ treatment (1 ml/kg i.p., sacrifice 48 hours thereafter). The other reference drugs had either little or no protective effects in these models. Laboratory tests for bilirubin showed that SGOT and SGPT fully correlated with the macro/microscopical findings. Thus, NaBPC157 can be used for the treatment of liver diseases. In addition, myelosuppression caused by irradiation is a reproducible model for studying the dynamics of recovering hematopoetic elements. NaBPC157 shows beneficial effects on bone marrow damages induced by sub-lethal irradiation.

Thus, NaBPC157 can be used for the treatment of bone marrow damages induced by irradiation. Considering the generally recognized relationship of $CCl_4$ with free radical formation and lesion development, the beneficial effects of NaBPC157 appear also to apply to other free radical induced organ lesions, in particular, irradiation.

EXAMPLE 19

Catecholaminergic System
Introduction:

The indirectly acting sympathomimetic drugs, like amphetamines, have common properties such as causing both increased catecholamine release and the inhibition of catecholamine re-uptake (primarily dopamine) at nerve endings in the Central Nervous System (CNS). Stereotyped behavior appears as a result of the activation of the dopaminergic system in the corpus striatum. It is generally believed that an increased amphetamine climbing behavior is a result of striatal dopamine receptor upregulation following dopamine antagonist haloperidol application. This subsequently causes amphetamine supersensitivity development. The application of NaBPC157 does not affect gross behavior or induce stereotypes.
Material and Methods:

The effects of NaBPC157 on the dopamine agonist amphetamine (10 mg/kg i.p.) stereotypes and on excitability were studied. NaBPC157 was applied as a prophylactic co-treatment or therapeutic salutary regimen (10 $\mu$g or 10 ng/kg i.p.). The stereotyped behaviour and excitability was induced in rats.
Results:

A marked attenuation and reversal (medication at the maximum of amphetamine-disturbances) of both stereotyped behavior and increased excitability (i.e., stronger and violent twitching, panic jumping and escaping) were regularly noted. Further focus was on the effects of NaBPC157 on the increased climbing behavior in mice. The mice were pretreated with dopamine antagonist haloperidol (5.0 mg/kg i.p.) and subsequently treated with amphetamine (20 mg/kg i.p. challenge 1, 2, 4 and 10 days after haloperidol pretreatment), which is usually used for the study of behavioral supersensitivity to an amphetamine stimulating effect. Thus, if the antagonization of the amphetamine stereotypes would appear as a result of a dopamine antagonist activity (direct or indirect) of the tested NaBPC157, a potentiation of the haloperidol increasing effect on amphetamine climbing behavior would be expected. Unlike this, an almost complete counteraction was noted when NaBPC157 was coadministered with haloperidol. Together, these data provide evidence for an interaction of NaBPC157 with the dopamine system. Furthermore, interaction of NaBPC157 with the central dopamine system was also shown in other experimental models (i.e., protection against stress ulcers). An interaction with the dopamine system has already been noted for many known peptides (neurotensin, CCK, etc.). In addition, the application of NaBPC157 reverses behavioral disturbances induced by LSD (e.g. 0.3 mg/kg i.p.) as well. NaBPC157 has a modulatory effect on the dopamine system. In the condition of increased dopamine release and synthesis induced by amphetamine, NaBPC157 could both prevent and reverse the consequent disturbances (i.e., stereotyped behavior). Similarly, NaBPC157 could markedly attenuate the consequence of dopamine receptors blocked by haloperidol. This suggests that the modulatory effect of NaBPC157 involves also a substitution of the otherwise prominent insufficient dopamine system. This avoids the subsequent supersensitivity of the dopamine receptors and the raised amphetamine disturbances.

Thus, NaBPC157 is a useful agent for the treatment of schizophrenia, amphetamine challenge effects (schizophrenia form psychosis) and drug abuse.

EXAMPLE 20

Stress

Introduction:

Stress is defined as a non-specific event leading to injuries in various organs. The stress response is defined as a response directed against various noxious events. One of the most frequently employed animal stress models is the restraint stress model leading to severe stress gastric lesions in rats. Other organs could also be affected.

Materials, Methods and Results:

Applied in a dose of 10 μg or 10 ng/kg b.w., i.p. or i.g., 1 hour before stress induction, NaBPC157 strongly prevented the otherwise inescapable development of severe gastric lesions. If the time between application of stress-reducing agents and stress induction (in the following text referred to as "period") is prolonged, the standard anti-ulcer agents become practically ineffective, strongly contrasting with the clear efficacy of the tested NaBPC157. NaBPC157 maintained its salutary activity even after an extremely prolonged period of 48 hours. The protection conferred by NaBPC157 includes the attenuation of lesions otherwise regularly appearing in other organs (e.g. liver, adrenal gland, kidney, testis, heart, pancreas, spleen). Thus, since the other generally known stress parameters are apparently less disturbed (i.e., thymolymphatic involution and cortical hypertrophy of the adrenal glands), it is evident that NaBPC157 could be applied in various stress conditions. NaBPC157 has a positive salutary impact on various lesions appearing in different organs regularly connected with non-specific stress pathology. Considering the same chain of events in humans as in the models used, this is even more emphasized because NaBPC157 has a salutary effect even if applied when stress pathology is already advanced (e.g. 24 hours after stress induction).

EXAMPLE 21

Demonstration of a Cytoprotective Effect

Introduction:

Cytoprotection was originally defined as a property to defend the cells against different noxious agents, an effect pointed out in gastric mucosa as a gastric acid independent effect. Later, this definition was extended to include essentially similar protective effects outside the gastrointestinal tract involving the lesions of different organs (cytoprotection-organoprotection). The possible cytoprotective effects of the application of NaBPC157 were studied based on their effect on the initial Robert's model for a cytoprotective-agent screening of the ethanol-induced gastric lesions.

Materials, Methods and Results:

NaBPC157 (10 μg or 10 ng/kg i.p.) has a prophylactic effect (applied either 1 hour before, or simultaneously with 96% ethanol (1 ml/rat, i.g.)) and a salutary effect (applied 1 hour after ethanol at the maximum of the lesion's development).

To create an acid-free environment for cytoprotection studies, a total gastrectomy was done 24 hours before the ulcerogenic procedure. In the absence of stomach and gastric acid, the damaging effects of cysteamine (400 mg/kg s.c., sacrifice 24 hours thereafter), so far thought to be an acid related duodenal ulcerogen, and the cytoprotective effects of NaBPC157 (10 μg or 10 ng/kg i.p.) were further challenged in comparison with reference agents (cimetidine (50), ranitidine (10), omeprazole (10), bromocriptine (10) and atropine (10) (values given in mg/kg i.p., 1 hour before cysteamine)) known also to be cytoprotective. In naive rats with an intact stomach, all of the applied substances had a strong beneficial effect. In gastrectomized animals the application of the investigated agents (i.e., NaBPC157 or the reference agents before cysteamine) significantly prevented the otherwise severe duodenal lesion development noted in the control gastrectomized cysteamine rats. In the groups not treated with cysteamine, no lesions were noted (laparatomy and gastrectomy only 24 hours or 48 hours post-surgical period) nor was lesion potentiation observed in cysteamine treated laparatomized animals. These findings (equal damaging effect of cysteamine, equal protection of NaBPC157 and reference agents in gastrectomized rats with intact stomach and without stomach, the damaging or protective effect is not related to gastric acid secretion) are indicative of a cytoprotective effect. An analogy (lesions not related to gastric acid) between the gastric (e.g. ethanol) and the cysteamine duodenal injuries is clearly suggested. A high "cytoprotective capacity", apparently acid independent, common for all tested agents but clearly more prominent for NaBPC157 is evident.

Because NaBPC157 was effective in much lower doses than other agents (i.e. μg or ng/kg vs. mg/kg), its effectiveness (and therapeutical application) can be extended to different organ lesions. This is due to the fact that the effectiveness of other agents in other organs is also suggested due to their "cytoprotective" effects (e.g. somatostatin: lesions of the adrenal gland, pancreas, liver, lung and gastrointestinal tract).

EXAMPLE 22

Demonstration of an Organo-protective Effect

Introduction:

For a useful extension of the "cytoprotective" effect into an "organo-protective" effect the investigation of endothelium protection is generally accepted. As a clear indication, the Monastral Blue studies in ethanol damaged gastric rat mucosa are widely recognized due to the ability of Monastral Blue to bind to damaged endothelium.

Materials and Methods:

All rats received Monastral blue (MB) (Sigma Company, USA) (1.0 ml/kg b.w., i.v.) 3 minutes before ethanol and the animals were sacrificed 1 minute after ethanol treatment. NaBPC157 (10.0 μg/kg i.p.) or saline (5.0 ml/kg i.p.) was given 1 hour before ethanol. Immediately after the sacrifice the stomach was removed and the lesions were assessed by unbiased observers as described before. Representative sections of the stomach and duodenum were processed for further histologic analysis. Vascular injury in the early period (1 minute after ethanol treatment) was assessed using the Monastral Blue technique. The areal density of stained mucosa was examined by TEM.

Results:

A strong reduction of MB-staining was consistently noted in groups treated with NaBPC157. Furthermore, no negative effects were noted with the application of NaBPC157. No influence on different basal parameters and no toxicity were observed, despite application of high dosages (e.g. g/kg b.w., i.p.).

Considering the widespread presence of endothelial vasculature tissue in the body and the crucial role of endothelium protection for organo-protective effects, NaBPC157 can be used as an organo-protective agent in different organ lesions.

EXAMPLE 23

Acute Pancreatitis

Materials and Methods:

NaBPC157 was tested in rats as a protective or therapeutic agent for acute pancreatitis (induced by bile duct ligation). At the same time, the influence of NaBPC157 on concomitantly developed gastric and duodenal lesions was investigated.

NaBPC157 (10 µg or 10 ng/kg b.w., i.p., i.g.) was given prophylactically 1 hour before ligation, whereas the therapy was conducted by a daily application 1 day after ligation (last application 24 hours before sacrifice). The effect was investigated at daily intervals until the end of the fifth post-ligation day.

Results:

In the pre-treatment application, a strong pancreatic protection was obtained. When applied in the condition of the already established severe acute pancreatitis, an obvious salutary effect was consistently noted. Assessing the appearance of the necrosis, edema, neutrophils and mononuclears, consistently less necrosis, edema and neutrophils, but more mononuclears were found in NaBPC157 treated rats. In studies of the serum amylase values relative to control data, a markedly lower rise (NaBPC157 pre-treatment application) as well as a detriment of the already raised values (NaBPC157 therapy application) was noted. Along with its beneficial effect on pancreatitis, a positive influence of NaBPC157 on gastric and duodenal lesion course in bile duct ligated rats was noted in both pre- and post-treatment applications. Taken together, NaBPC157 can be used for the treatment of acute pancreatitis with an additional positive impact on concomitant gastroduodenal pathology.

EXAMPLE 24

Effects on Cardiotoxicity

Materials and Methods:

The experiments were conducted on Albino Wistar rats and Hartley guinea pigs. Cardiotoxicity was induced by administration of a barium chloride solution (10 mg/kg b.w.), desipramine (10 mg/kg), digitalis (total dose 6.5 mg/kg) and isoprenaline (15 mg/kg) through a jugular venous cannula. In addition, doxorubicin was applied in multiple dosages (3 mg/kg s.c., once weekly through 13 weeks) and in single dosages (7 mg/kg, i.v.) and provoked cardiomyopathy. Cardiotoxicity was also induced by an immobilization stress as non-pharmacological myocardial damage. NaBPC157 was administered as indicated below:

1. Barium chloride
   a) pre-treatment (one hour before): NaBPC157 50 µg/kg, 10 µg/kg and 10 ng/kg, intraperitoneally;
   b) post-treatment (after 60 seconds): NaBPC157 10 µg/kg and 10 ng/kg, intravenously;
2. Desipramine: NaBPC157 50 µg/kg and 50 ng/kg, intraperitoneally one hour before;
3. Digitalis: NaBPC157 50 µg/kg and 50 ng/kg, intravenously at 15 minute intervals;
4. Isoprenaline: NaBPC157 50 µg/kg and 50 ng/kg, intravenously 15 minutes before;
5. Immobilization stress: NaBPC157 10 µg/kg and 10 ng/kg, intraperitoneally one hour before and immediately after the tying, and at 24 and 48 hours of immobilization;
6. (a) Chronic doxorubicin toxicity: NaBPC157 10 µg/kg and 10 ng/kg, intraperitoneally concomitantly with doxorubicin;

(b) Acute doxorubicin toxicity: NaBPC157 10 µg/kg and 10 ng/kg, intraperitoneally one hour before doxorubin.

In arrhythmia models, an electrocardiogram was continuously recorded on anesthetized animals. Every 15 seconds or when rhythm disturbances occurred, extended recordings were made at 50 mm/s or 100 mm/s. In other models, an electrocardiogram was recorded once or repeatedly with animals briefly anesthetized with a paper speed of 50 mm/s in extended recordings. Doxorubicin toxicity was evaluated by macroscopic and microscopic examination of the heart and other organs by biochemical analyses. A similar procedure was applied in the immobilization stress tests.

Results:

An antiarrhythmic effect of NaBPC157 in the model of barium chloride-induced arrhythmias was noted. In the pre-treatment studies, NaBPC157 delayed and prevented the arrhythmia occurrence and reduced and/or prevented ischemia. In the post-treatment studies, NaBPC157 caused rapid conversion to sinus rhythm and prevented arrhythmia recurrence.

NaBPC157 completely prevented sudden decrease in heart rate and conduction disturbances induced by desipramin (PQ prolongation and QRS widening). NaBPC157 also prevented ventricular tachycardia associated with the proarrhythmic effect of desipramin and severe atrioventricular block. The effect is dose-dependent.

Furthermore, NaBPC157 has selective effects on digitalis-induced cardiotoxicity. NaBPC157 exhibited positive effects on sudden decrease in heart rate and rhythm disturbances (ventricular extrasystole, ventricular tachycardia and atrioventricular block) by means of preventing or attenuating them. The effect of NaBPC157 in ng doses on the slowing of conduction induced by a toxic dose of digitalis was not significant. The effect was more pronounced with microgram doses of NaBPC157.

NaBPC157 clearly prevented ischemia and myocardial infarction. The effect was more pronounced with microgram dosages. Single intraperitoneal administration of NaBPC157 in the form of a pre-treatment resulted in prevention of electrocardiographically demonstrated ischemia and histological myocardial damage during the immobilization stress test. Post-treatment administration of NaBPC157 in already overt electrocardiographic changes also relieved ischemia. Microgram dosages of NaBPC157 resulted in an increase in voltage of the QRS complex, particularly in a pre-treatment application.

The application of NaBPC157 leads to significantly reduced pathomorphological findings of antracyclin cardiomyopathy (severe damage of myocytes and vessel walls, and vacuolisation) after single, and in greater extent, after multiple doxorubicin administration. The LDH activity is significantly decreased, in spite of markedly elevated absolute values.

Summarizing, NaBPC157 proves useful as an antiarrhythmic, antianginal and cardioprotective agent.

EXAMPLE 25

Antidepressant Activity

Materials and Methods:

Various antidepressants have antiulcer activity and the models currently used in ulcer and depression research share a considerable degree of similarity. Therefore, the possibility that depression disorders could be effectively influenced by a primary antiulcer agent with cyto-/organo-protective activity such as NaBPC157 was investigated in two rat depression assays: the forced swimming test (a Porsolt's procedure) and the chronic unpredictable stress method (after five days of unpredictable stress protocol, once-daily drug application during the stress procedure and an open field-immobility test assessment at fourth and sixth days of medication).

Results:

In the forced swimming test a reduction of the immobility time in the NaBPC157 (10 μg, 10 ng, 10 μg/kg, i.p.) treated rats corresponded to the activity of animals treated with 15 mg or 40 mg (i.p.) of the conventional antidepressants, imipramine or nialamide, respectively. A further aggravation of experimental conditions in chronic unpredictable stress procedure led to a failure of imipramine activity (30 mg), whereas NaBPC157 (10 μg, 10 ng) dose-dependently improved the mobility in chronically stressed rats.

EXAMPLE 26

Parkinson's Disease Models

Materials and Methods:

Parkinsongenic agents, 1-methyl-4-phenyl-1, 2, 3, 6-tetrahydropyridine (MPTP) (known to destroy the dopamine nigrostriatal system by formation of free radicals) (30.0 mg/kg b.w., i.p. once daily for 6 days and after 4 days once 50.0 mg/kg b.w., i.p.) or reserpine (a catecholamine vesicles depletor) (5.0 mg/kg b.w., i.p.) were applied. NaBPC157 (1.50 μg or 15.0 ng/kg b.w., i.p.) was applied 15 minutes before or alternatively 15 minutes after each MPTP administration. In reserpine studies, NaBPC157 (10.0 μg or 10.0 ng/kg b.w., i.p.) was given either 15 minutes before reserpine or in the already established complete catalepsy 24 hours thereafter.

Results:

NaBPC157 strongly improved the MPTP-impaired somatosensory orientation and reduced the MPTP-induced hyperactivity. Furthermore, NaBPC157 reduced MPTP-motor abnormalities (tremor, akinesia, catalepsy, otherwise very prominent in saline control) leading to an almost complete abolition of the normally lethal course of MPTP treatment in controls. In reserpine experiments, NaBPC157 strongly prevented the development of the otherwise very prominent catalepsy. When applied 24 hours thereafter, NaBPC157 reversed the established catalepsy. Supportingly, a reduction of reserpine-hypothermia (NaBPC157 pre-treatment) and reversal of further prominent temperature fall (NaBPC157 post-treatment) have been consistently observed.

Both of the above used common animal models are known as being indicative for human disturbances and their therapy. Due to the fact that a high effectiveness was demonstrated in pre- and post-treatment studies under , μg and ng regimens, NaBPC157 appears to be well suited for use in the treatment of Parkinson's disease and Parkinson's disease-like pathologies.

Furthermore, the observed effect in reserpine hypothermia allows the conclusion that NaBPC157 is well suited for the therapy of temperature disturbances.

EXAMPLE 27

Effects on the Healing of Bone Defects

Materials and Methods:

The osteogenic effect of bone marrow and TRIS-BPC157 on the healing of segmental bone defects was studied in 42 rabbits for six post-operative weeks. Following injury induction (a 0.8 centimeter osteoperiosteal defect was created in the middle of both radii), the experiments using bone marrow and the TRIS-BPC157 (6 rabbits per group) were carried out as follows: Saline (2 ml intramuscularly and 2 ml locally into each of the bone defects) treated injured animals were used as controls (group 1). In the second and third group each of the bone defects was treated locally with either 2 ml autologous bone marrow ($7^{th}$ post-operative day) or TRIS-BPC157 (10 μg/kg b.w. $7^{th}$ and $14^{th}$ post-operative days). In groups four, five and six TRIS-BPC157 was applied intramuscularly (i.m.) either at the $7^{th}$, $9^{th}$, $14^{th}$ and $16^{th}$ post-operative day (10 μg/kg b.w. ) or once daily in the period of the $7^{th}$–$21^{st}$ post-operative days (10 μg or 10 ng/kg b.w.). As a standard treatment immediately after its formation, the bone defects of the seventh group were filled with an autologous cortical graft.

All animals were sacrificed in the sixth post-operative week. Segmental defect healing was evaluated with bi-weekly radiographs and histological examinations.

Results:

The parallel comparison of radiographs taken in four time intervals (callus surface, microphotodensitometry of the bone defect) and quantitative histomorphometry revealed that bone marrow injected locally into the bone defect and TRIS-BPC157 applied intramuscularly (particularly in a daily dose of 10 μg/kg b.w. during the 14 day period) significantly improved bone healing (p<0.001). The effect corresponds to the effect of the autologous cortical graft.

Considering the clinical relevance of this study, bone marrow and TRIS-BPC157 (particularly in a daily dose of 10 μpg/kg b.w. during 14 days) elicited healing of bone defects. Due to its simple administration and the low risk of complications, autologous bone marrow applied locally and, in particular, intramuscularly administered osteogenous substances such as TRIS-BPC157, are advantageous over other more complex surgical methods (i.e., bone grafts, vascularized bone grafts, method of llizarov) for the treatment of healing impairments in humans.

EXAMPLE 28

Effect on Wound Healing

Materials and Methods:

NaBPC157 was used in order to establish its influence on different elements connected with the healing process. Elements thought to be of importance in the process of healing are the formation of granulation tissue, angiogenesis and the production of collagen. The influence of NaBPC157 on the formation of granulation tissue, collagen formation, and angiogenesis as well as tensile strength development was tested using three experimental rat models: 1) Skin incisional wounds 2) Colon-colon anastomoses and 3) Esophago-duodenal anastomoses. The specimens were histologically assessed for collagen, reticulin and blood vessels using scoring and morphometry methods.

Results:

In all experiments significant differences between NaBPC157 treated rats and controls were found. The experiments demonstrate a strong, promoting involvement of NaBPC157 in the healing process. These effects were achieved by different routes of application including intragastric and local application. Furthermore, the assessment of the tensile strength consistently revealed increased values in NaBPC157 treated rats.

Based on a close similarity between the animal model and corresponding human disturbances and the high degree of similarity between the healing processes in rats and humans, NaBPC157 can be used in a therapy for wound healing in humans.

EXAMPLE 29

Effect on Respiratory Disturbances

Materials and Methods:

Guinea pigs (Hartley, both sexes, 500–700 g b.w.) with whole body plethysmography, urethane anesthesia (1.5 g/kg i.p.), artificial ventilation under constant pressure (0.98 kPa), and relaxation of skeleton musculature by suxamethonium (0.2 mg/kg i.v.) were used in the present experiments. The inflation volume (mm, means±SD) was assessed before and after application of spasmogens (histamine, serotonin, acetylcholine, bradykinine, i.v.) or NaBPC157 (10 minutes before repeated spasmogen application, i.v.).

Results:

A decrease of inflation volume induced by serotonin, histamine, acetylcholine and bradykinine was inhibited by NaBPC157 (10 μg/kg b.w., i.v. and/or 10 ng/kg b.w., i.v.).

Based on the observed salutary effect of NaBPC157 on bronchoconstriction induced by various spasmogens and the known close similarity between the used model and human conditions, a successful application of NaBPC157 is evident in treating various disorders connected with bronchoconstriction and/or disturbances of the respiratory tract.

EXAMPLE 30

Effect on Pulmonary Hypertension Syndrome

Materials and Methods:

The present experiments describe the effects of nitric oxide (NO) agonists and antagonists and the influence of NaBPC157 on the development of Pulmonary Hypertension Syndrome (PHS) and tissue lesions in chicks. Experiments investigating acute toxicity were conducted. These included single dose applications of saline (1 ml i.p.), NaBPC157 (10 μg/kg b.w.), L-NAME (NO antagonist/doses 50, 100, 150 mg/kg b.w.) and L-arginine (NO agonist/100 mg/kg b.w./ with their combination (L-NAME+NaBPC157, L-NAME+ L-arginine)). Pathohistological examinations of the spleen, heart, liver and lungs and hematological analyses were conducted. Furthermore, chronic toxicity experiments were conducted. The animals were treated daily during five weeks with L-NAME (10 mg/kg b.w.), L-arginine (100 mg/kg b.w.), NaBPC157 (10 μg/kg b.w.) and their combinations (L-NAME+NaBPC157, L-NAME+L-arginine) intraperitoneally. Seven animals from each group including controls (saline 1 ml i.p.) were sacrificed every week.

Results:

The application of L-NAME caused PHS in the treated chicks. This effect was prevented by the simultaneous application of L-arginine and NaBPC157. Pathohistological examinations of both acute and chronic toxicity revealed that L-NAME caused severe tissue damage (myocardial and hepatic cell necrosis, and necrosis of the lymphoid cells in the spleen) while L-arginine provoked predominantly congestion, edema and hemorrhages in all organs. Hematological analyses showed significant hemoglobin and leukocyte number decreases in the L-NAME treated groups of chicks. The effects of L-NAME were successfully inhibited by the application of L-arginine and NaBPC157. NaBPC157 did not cause any tissue or organ damage.

Considering the similarity of the above used animal model and the corresponding human disturbances, NaBPC157 can be used for the therapy of Pulmonary Hypertension Syndrome. Furthermore, its useful application in commercial breeding is evident.

EXAMPLE 31

Experimental Hypertension

Materials, Methods and Results:

In hypertensive animals (Goldblatt hypertension) with two kidneys (2K1C) or with one kidney (1K1C) NaBPC157 decreased blood pressure quickly (e.g. 5 or 10 minutes post-injection). This effect lasted 20 minutes in 1K1C rats or 12 hours, at least, in 2K1C animals. The effect was repeatedly obtained after a second or third application 24–48 hours thereafter. Similarly, in rats fed with either a high fructose (80%) or a high salt (15%) diet for a prolonged period, NaBPC157 markedly reduced the otherwise continuously raised blood pressure values toward normal values. The therapeutic effect is long lasting, and a tolerance was not developed even after a six-month period. No influence of NaBPC157 on basal blood pressure values was noted.

In addition to a decrease of the otherwise raised blood pressure values, NaBPC157 also caused a marked attenuation or even abolition of the lesions and disturbances normally appearing in the various organs which were (after three weeks of an increased salt diet in the controls): very severe hyaline degeneration with prominent parenhymaous hemorrhages, degeneration of the arterial walls, vacuolisation of the cells in the heart, severe congestion (specifically medullar) in the adrenals, severe congestion, parenhymatous hemorrhage with hematuria in kidney and hemosiderosis and erythrocytophagia in the spleen. The vessels were much less damaged in the NaBPC157 treated rats in addition to less vacuolisation of the wall and the absence of hemorrhaging. Furthermore, a clear protection against fundus damage was evidenced consistently in NaBPC157 treated rats.

Using different models of animal hypertension, NaBPC157, given as 10 μg or 10 ng/kg b.w., i.v., i.p. or i.g., achieved consistent results within different regimens. Considering the apparent similarity of these models with corresponding human conditions, NaBPC157 can be used for the treatment of hypertension and various organ damages caused by hypertension.

EXAMPLE 32

Effect on Bleeding Time

Materials and Methods:

The effect of 2-AMP-BPC157 on bleeding time in mice and rats (with and without heparin pre-treatment) was investigated in conjunction with the in vitro activity on clotting parameters in human blood.

Results:

In basal conditions (2-AMP-BPC157, 10 μg, 10 ng, 10 μg, 1 μg, 10 fg/kg b.w., i.p. simultaneously with tail cutting) a strong dose-dependent bleeding time reduction was consistently demonstrated in both mice and rats. In heparin (1000 lU/kg i.p.) pre-treatment studies (2 hours before bleeding initiation), a prominent reduction of the otherwise strongly increased bleeding time was regularly noted in 2-AMP-BPC157 treated animals with either 10 μg or 10 ng/kg b.w., i.p. No influence (2-AMP-BPC157 in concentration of 10 μg/ml, incubation 1 hour) on clotting parameters in human blood was demonstrated in vitro. Thus, an effect on the endothelial layer is suggested.

Considering the close similarity of the bleeding mechanisms in humans and animals and the widely recognized significance of the models used for agent screening, 2-AMP-BPC157 can be used for the treatment of disturbed coagulation (e.g. heparinization).

EXAMPLE 33

Effect on Experimental Diabetes

Materials, Methods and Results:

When given intraperitoneally (i.e., 10 µg/kg b.w.), NaBPC157 was shown to prevent the development of alloxan as well as streptozotocin induced diabetes in rats. A decreased glucosuria and fewer island lesions were found during 14 days. In our preliminary experiments, NaBPC157 was also effective when applied in the presence of the already established 14 day alloxan lesions. In further experiments, the antidiabetic effects of NaBPC157 were further investigated with particular focus on their possible activity when applied intragastrically. NaBPC157 (dosage of 10 µg and 10 ng/kg b.w.) was combined with an alloxan application of 300 mg/kg s.c. or 200 mg/kg b.w., s.c., in pre-(24 hours or 1 hour before alloxan application), co- and post-(48 hours following alloxan application) treatments. In general, NaBPC157 decreased the raised glucose serum levels and significantly increased the survival of alloxan treated animals (the effect was particularly obvious in groups treated with the higher dosage of alloxan). Interestingly, in addition to raised glucose serum levels in alloxan treated animals, an exaggerated appearance of gastric lesions was noted in control diabetic rats. Each of the NaBPC157 regimens significantly decreased ulcer severity regardless of treatment conditions. Essentially, the same results were obtained in mice.

Considering the similarity between human pathology and the models used and in view of their widespread use for the screening of agent activity, NaBPC157 can be used for the treatment of diabetes.

EXAMPLE 34

The Anti-Nociceptive Effects

Materials and Methods:

The anti-nociceptive effects of NaBPC157 were evaluated in comparison with aspirin and morphine reference standards in various experimental models of indirect/direct nociception and neurotoxicity: writhing (acetic acid/magnesium sulfate), tail pinching, hot-plate, and capsaicin application.

Results:

NaBPC157 (administered either in the ng or µg/kg range, i.p.) significantly reduced the reactions in the writhing (inflammatory and non-inflammatory, prostaglandin-dependent and independent) and tail pinching tests. In the hot-plate test, NaBPC157, unlike morphine, had no effect on normal animals. Furthermore, NaBPC157 was administered in the form of a pre-treatment or once daily for 14 days after a capsaicin injection. In the tests, NaBPC157 strongly reduced capsaicin-allodynia. This reduction in the effect of capsaicin could not be obtained when NaBPC157 was applied in the presence of established capsaicin-somatosensory neuron degeneration (application only on the 14$^{th}$ day after capsaicin). Thus, since otherwise inescapable somatoneuron depletion following a capsaicin application could completely be avoided with a daily NaBPC157 application, it is possible that the effects of NaBPC157 could be related specifically to the integrity of capsaicin sensitive somatosensory neurons and their protection (i.e., primary afferent neurons having small diameter somata and unmyelinated (C-) or thinly myelinated (A-δ) fibers).

Considering that capsaicin would induce essentially the same disturbances in both humans and animals, NaBPC157 can be used for the treatment of various pain disturbances as well as in conditions followed by somatosensory neuron function impairment.

EXAMPLE 35

The Effect on Convulsions

Materials and Methods

The effects of KBPC157 on convulsions induced by bicucculine, picrotoxine, strychnine and isoniazide were examined. KBPC157 (100 µg, 10 µg or 10 ng/kg b.w.) was applied (i.p.) simultaneously or 15 minutes before application of the convulsive agents (mg/kg b.w., i.p.) picrotoxine (3), strychnine (6, 3 or 1.5), bicucculine (2.5) and isoniazide (800 mg).

Results:

KBPC157 produced a consistently positive (dose and time dependent) anti-convulsive effect against all of the applied convulsants. Considering the similarity of the models used with human conditions, KBPC157 can be used for the treatment of convulsion disorders.

EXAMPLE 36

Spinal Cord Injury

Materials and Methods:

Spinal cord injury was induced in male Albino Wistar rats by controlled pressure (a vascular clip Aesulap 0.10–0.15 N) on the exposed spinal cord (at the level of Th12) for 30 seconds. The animals were treated immediately after injury and once daily until the 10$^{th}$ day following injury with NaBPC157 (10 µg, 10 ng/kg b.w., i.p.) or saline. The animals were sacrificed 24 hours following the last application.

Results:

A careful investigation was conducted both clinically (assessed daily, score 1–5) and microscopically. It revealed a strong attenuation of otherwise sustained paralysis (in control rats) in the rats treated with NaBPC157. Considering the similarity of the used models with human conditions, NaBPC157 can be used in the therapy of spinal cord injuries.

EXAMPLE 37

Chronic Alcohol Intoxication

Materials and Methods:

The effects of NaBPC157 on chronic alcohol intoxication were examined. Male Albino Wistar rats were used for these experiments. The rats were drinking either commercial whiskey or ethanol (10–20% water solution) for three months. The application of NaBPC157 (10 µg, 10 ng/kg b.w.), propranolol (10 mg/kg b.w.), and ranitidine (10 mg/kg b.w.) (control rats received an equivolume of saline 5.0 ml/kg), either intragastrically or intraperitoneally, was conducted either prophylactically (10 days before alcohol initiation) or as a co-treatment together with alcohol or therapeutically (starting at the end of a two month period, i.e. during the last month of the experiment).

Results:

A direct assessment of the blood pressure in the portal vein clearly showed that NaBPC157, as well as propranolol (given in all of the regimens), markedly prevented and/or decreased the otherwise increased portal blood pressure values in control rats. By contrast, ranidine therapy led to even more increased portal pressure values than those present in control animals. Furthermore, more than propranolol, NaBPC157 was able to markedly attenuate the otherwise advanced lesions in the stomach of the alcohol treated rats. A similar beneficial effect was also noted on other organ lesions (i.e., kidney, heart).

Considering these consistent positive effects and the generally known evidence that increased alcohol intake produces similar changes in humans, it is evident that NaBPC157 is useful in the therapy of alcohol injuries.

EXAMPLE 38

The Effects on the Brain Ischemic Disorders
Materials and Methods:

NaBPC157 (10 µg or 10 ng/kg b.w., i.p.) or saline (5.0 ml/kg b.w., i.p.) was applied either 1 hour before or 1 hour after both carotid arteries were ligated for 3 or 6 hours in rats.

Results:

A strong positive effect of NaBPC157 is evident in both pre-treatment (1 hour before ligation) as well as post-treatment (1 hour after ligation) applications. This was the case in both µg and ng ranges and in both three or six hours studies. Apart from the score values, severe perivascular and brain tissue edema with brain congestion were the most distinct and characteristic findings. Also the areas of demyelinization were noted, especially in the cerebellum. All of these features were much less pronounced in the NaBPC157 treated groups of animals regardless of the treatment conditions.

Considering the severe ischemic lesions noted in the controls and an apparent similarity between ischemic disorders in rats and humans, a favorable application of NaBPC157 for treating brain ischemic disorders in humans is apparent.

EXAMPLE 39

Effect on Nerve Injury
Materials and Methods:

The effect of NaBPC157 on peripheral nerve regeneration was examined. In anaesthetized adult male Wistar rats (225–250 g), the right sciatic nerve was exposed, cleared of connective tissue and transected 5 cm distally to the sciatic notch. Three perinueral sutures (10.0 Ethilon, Ethicon) were used for the anastomosis ensuring proper fascicular alignment. Animals were treated either locally on the site of the anastomosis by a bath of 1 ml of NaBPC157 (2 µg/ml or 2 ng/ml), intragastrically or intraperitoneally (10 µg or 10 ng/kg b.w.) immediately after anastomosis formation. Controls received an equivolume of saline. On the indicated postsurgical days (days 3, 6, 9, 12, and 30), functional tests were performed. These tests included a hot water test (60° C.), cold water test (2° C.), walking track analysis, EMG-distal latency, and amplitude of CMAP. The specimens for histological and morphometric analyses were taken as well. In the other experiments using the same surgical procedure and the same site of the nerve, a crush injury with microsurgical forceps was induced for 60 seconds and NaBPC157 was applied locally. The assessment was conducted after 2, 7, 10, 50, and 100 days.

Results:

Assessed either clinically or microscopically, particularly in the early period, the application of NaBPC157 markedly improved the healing of the injured rats.

Considering the close similarity between the animal injury and human conditions, NaBPC157 can be used for the therapy of peripheral nerve injury.

EXAMPLE 40

Effect on Neuroleptic Disturbances

The effect of NaBPC157 on various neuroleptic induced disturbances was examined.
Materials, Methods and Results:

Application of NaBPC157 (10 µg or 10 ng/kg b.w., i.p.) consistently attenuated the haloperidol and fluphenazine (haloperidol 0.625, 1.25, 2.5, 5.0 and 10.0 mg/kg b.w., i.p., fluphenazine 0.3125, 0.625, 1.25, 2.5 and 5.0 mg/kg b.w., i.p. (4.0 ml/kg)) catalepsy at lower dosages of both neuroleptics in subsequent time intervals. In addition to the salutary effect on the lower doses of neuroleptics, an even stronger beneficial anticataleptic effect of NaBPC157 appears with a higher dosage of both neuroleptics observed with both µg and ng doses of NaBPC157. This effect was also noted in somatosensory orientation of sulpiride (20, 40, 80, and 160 mg/kg b.w., i.p.) treated animals, although no catalepsy could be observed in control sulpiride mice.

The favorable application of NaBPC157 in treating disorders connected with dopamine systems, cataleptic disorders and neuroleptic disturbances is evident.

EXAMPLE 41

Application in the Therapy of Shock
Materials and Methods:

Experimental hemorrhagic shock was investigated in anesthetized rats (cannulas in a common carotid artery and in a jugular vein). A controlled blood volume removal was conducted until the death or stabilized low blood pressure (30–35 mm Hg). In these experiments, CaBPC157 (10 µg or 10 ng/kg b.w.) or saline was given intraperitoneally (5.0 ml/kg) 15 minutes before bleeding or intravenously (3.0 ml/kg) after a period of 5 minutes of stable low blood pressure.

Results:

Relative to the control values, a significantly higher blood volume loss sustained before the death (which is dose-dependent) was consistently noted in CaBPC157 treated rats. In hypovolemic and hypotensive animals treated with CaBPC157, a prompt and long-lasting significant blood pressure increase without death was demonstrated. This contrasted with a short and weak blood pressure rise and a 75% death rate before the end of the 45 minute experimental period in the control group. In rats subjected only to surgery after anesthetization but not exanguated, CaBPC157 (i.p. or i.v.) administered after a 65 minute stabilization period did not significantly influence the arterial blood pressure values within the same post-application period. These data suggest that CaBPC157 could be effective in ameliorating the consequences of acute blood volume loss. Considering an apparent similarity between the used animal models and human disturbances, CaBPC157 can be used for the therapy of shock.

EXAMPLE 42

Effect on Abnormal Lymphocytes
Materials, Methods, and Results:

Immunologic findings in two female patients suffering from a rare clinical entity - hereditary eosinophilia associated with intraepidermal bullous dermatitis and subacute sclerosing panenciphalitis—were examined. The effects of NaBPC157 (in vitro) on lymphocyte chromosome aberrations and T cell proliferation were investigated. NaBPC157 induced a significant reduction of severe types of chromosome aberrations (i.e. normalized lymphocyte findings) and showed a stimulatory effect on mitosis cycles.

EXAMPLE 43

The Effect of Malformations
Materials and Methods:

The effect of NaBPC157 on vitamin A induced malformations in mice was examined. NaBPC157 (10 ng/kg b.w.

or 10 µg/kg b.w., i.p.) or saline (5 ml/kg b.w., i.p.) was given simultaneously with vitamin A (15,700 IU/kg b.w., i.m.) at the tenth day of pregnancy. Mice not treated with vitamin A, but receiving saline in the same dosage at the same time, were used as controls.

Results:

A number of malformations were induced by the application of vitamin A. A significant reduction in the number of malformations was observed in groups treated with NaBPC157. A favorable application of NaBPC157 in therapy of fetal disturbances is evident.

EXAMPLE 44

Ovariectomy

Materials and Methods:

A conventional ovariectomy was conducted. NaBPC157 was applied (10 µg or 10 ng/kg b.w., i.p.), either once daily for 28 days, or once daily for 14 days starting from the $15^{th}$ day post-ovariectomy. Regularly in prolonged regimen the last application was 24 hours before sacrifice. Other groups received a single µg-application on the $15^{th}$ day post ovariectomy. Five groups were used as controls: 2 groups were ovariectomized, treated with saline and sacrificed on the $15^{th}$ and $28^{th}$ day post-ovariectomy, 1 group was non-ovariectomized but treated with saline, and 2 non-ovariectomized groups were treated with NaBPC157 (10 µg or 10 ng/kg b.w., i.p.) once daily for 28 days. Vaginal smears were taken from each animal 5 minutes before surgery on days 9, 14, and 28 of the experiment and Pap stained for cytological evaluation. The degree of maturation of vaginal epithelium was expressed by the means of the maturation values. After the sacrifice, extremity bones were collected from each animal for the purpose of biomechanical testing as briefly described below.

Biomechanical Testing:

All bones were checked in dependence of different moments of bending (one point bending) (moment of bending=Nm) in different directions, anterior- posterior-, and latero-lateral. Femoral and tibial bones were used in this experiment. Distal parts of the bones were fixed with bone cement (Palacos) in 1 cm long metal tubes. Metal tubes were fixed in a loading system. The bones were kept humid continually. The length of the free part of the bone was measured, as well as the length from the fixing part to the loading point. The experiment was done according to the principle of bending a stick, fixed in one point, within limits of elasticity. The load was 0.1, 0.2, 0.5, 0.7, 1.0 N. Deformity, or angle of bending was measured as the angle of deflection of the laser beam that was refracted from a small mirror fixed at the end of the bone. The weight of the mirror was added to the applied bending force. The millimeter-paper at which the laser beam was directed was distanced about 1.5–1.8 m from the bone with the small mirror mounted on it. The angle of deformation was measured using a trigonometrical method. During every single loading, lasting of deformation (and subsequent recovery) was measured. After unloading, the bone returned to its starting position, evidencing that no structural changes were present in the bone and that loading was provided within the elasticity limits of Hook's diagram. This observation showed that it was possible to load the same bone twice in a different direction without changing its structure. If no additional deformity was observed during two subsequent minutes or if additional recovery was achieved, these points were estimated as final (in general, the time of measuring was approximately 30 seconds (ovariectomized control) or 16 minutes (healthy)). The bone angular deformity (loading and post-loading recovery) was expressed in mm/sec.

Results:

Daily treatment with both doses of NaBPC157 resulted in a noticeably increased maturation value compared with the atrophic decreased maturation value in untreated control rats. Thus, it is suggested that NaBPC157 is able to prevent vaginal atrophy in rats caused by castration.

In ovariectomized control groups the lowest amplitude of bending with the shortest time, as well as the lowest amplitude of returning was observed. The same low values were obtained in both control groups sacrificed either after 15 or 28 days. This was noted in both ovariectomized, saline-treated groups (sacrificed either on the $15^{th}$ or $28^{th}$ day). A positive tendency was observed in the group that received a single NaBPC157 µg-application on the $15^{th}$ day post ovariectomy. Significantly better results were obtained in all other groups treated with NaBPC157, either ng or µg. The best results were obtained in the group that received a daily NaBPC157-µg treatment for 28 days. All of the parameters in ovariectomized animals were markedly improved and the level of improvement tended to achieve the values noted in healthy groups. There was no difference noted between the healthy rats regardless of whether they were treated with saline or with NaBPC157 (µg or ng dosage).

Considering the generally accepted significance of these animal models for human ovariectomy conditions on both vaginal atrophy and osteoporosis development, it is evident NaBPC157 can be used in ovariectomy therapy.

EXAMPLE 45

Tumors

Materials, Methods and Results:

One of the commonly used models of experimental tumors involves the assessment of the number of the metastases of carcinoma and melanoma B-16 in mice. Like various models of experimental tumors, these experimental tumors share a considerable similarity with disturbances observed in human patients. Applied in different protocols, NaBPC157 was shown to decrease the number of metastases in treated mice relative to corresponding controls. Ehrlich's ascites tumor (EAT) is a tumor which can grow in all strains of mice. It can grow in ascitic or in solid form depending upon the way in which the tumor cells are administered. Although, generally, animal tumor models only partially share a similarity with human disease, the use of this model has achieved general acceptance because of its possible usefulness when applied in anti-tumor agent research.

Survival (days) in the mice injected with Ehrlich's ascites tumor cells was mostly limited to less than 25 days. Previous incubation of tumor cells with NaBPC157 (2 µg/ml) led to a prolonged life of the animals injected with said tumor cells. More than 90% of animals survived to the end of the 45-day observation period. In addition, various cytostatic drugs induced neutropenia in patients as well as in experimental animals. Cyclophosphamide is a commonly used agent for neutropenia induction. An application of cyclophosphamide (180 mg/kg i.p.) induced significant disturbances. NaBPC157 prevented neutropenia, decreased the reticulocytes and improved hemoglobin values.

Consequently, an anti-tumor potential of NaBPC157 is evident. Considering the apparent similarity of the animal models and human conditions and the beneficial effects obtained in both in vivo and in vitro experiments, NaBPC157 is useful in an anti-tumor therapy. NaBPC157 is suitable for the attenuation of the cytostatic noxious effects.

EXAMPLE 46

Anti-Viral Activity

Materials and Methods:

ARBO-viruses (Tick Born Encephalitis (TBE), Bhania, Dengue 1, 2, 3, 4, Sinbis, West Nile, Éalovo), Hepatitis A, Lymphatic Choriomeningitis (LCM) and Herpes type 1, were applied i.c. (or p.o. (post-operatively)—Hepatitis A) as virus suspensions, in a dilution of $10^{-2}$ (0.02 ml/mouse). NaBPC157 (20 µg/kg b.w.) or 0.9% NaCl (0.02 ml/mouse) was applied i.c. or i.p. a) in a pre-treatment regimen, b) simultaneously with the virus application or c) 4 days after infection in the presence of the established disease symptoms.

Results:

A significant delay of the onset of disease symptoms and consequent death (otherwise regularly appeared at $4^{th}$ and $5^{th}$ post-infection day in control animals) was noted after simultaneous application of NaBPC157 with the viruses. When given in the presence of a severe disease picture, a significant prolongation of survival time has been consistently noted. Evident was a complete lack of either symptoms or subsequent death after the NaBPC157 pre-treatment.

To verify the obtained results, the virulence of the applied virus suspensions (ARBO-virus infected) was also tested by inoculation of brain suspensions prepared from the mice which had been previously treated with NaBPC157 or saline and survived (NaBPC157) (despite virus application) or spontaneously died (saline), respectively. Unlike saline-brain suspension inoculated mice (which did not differ from virus-suspension inoculated saline treated mice), no disease symptoms or death was observed in NaBPC157-brain suspension inoculated mice. The mice were observed for 50 days following the brain suspensions inoculation.

The beneficial effects of NaBPC157 were resistant to an increased temperature (56° C. for 30 minutes) incubation.

Considering that these viruses induce similar disturbances in humans, NaBPC157 can be used in the therapy of viral diseases, especially in a therapy where the general condition is markedly impaired (e.g. AIDS and AIDS-related conditions).

EXAMPLE 47

Intestinal Lesions

Materials and Methods

The effects of NaBPC157 (10 µg or 10 ng/kg i.p., i.g.) were investigated in rats in comparison with several reference standards in several experimental ulcer models (48 hour-restraint stress, subcutaneous cysteamine, intragastrical 96% ethanol ulcer tests, NSAIAs-lesions, DNFB (Dinitrofluorhenzene), reflux esophagitis following esophagojejunal termino-lateral anastomosis) (pre-/co-/post-treatment).

Results:

Only NaBPC157 regimens were consistently effective in all of the tested models. Bromocriptine, amatadine, famotidine, cimetidine and somatostatin were ineffective (restraint stress) or only partially effective (bromocriptine, DNFB-intestinal lesions; sucralfate, ranitidine, cholestyramine, reflux esophagitis). Considering the reference peptides, a dose-dependent protection (cysteamine) and/or partial positive effect (related to treatment conditions) (ethanol) was obtained with glucagon, NPY and secretin, whereas CCK 126–30/ was not effective.

Considering that all of these models have been used for the screening of the agents currently used in the therapy of gastrointestinal lesions and the consistently beneficial effects of NaBPC157, its favorable application in the therapy of the lesions of the whole intestinal tract is evident.

EXAMPLE 48

Effect on Cognitive Disorders

Materials and Methods:

The application of anti-cholinergic agents (scopolamine, atropine, 10 mg/kg b.w., i.p.) led to a significant cognitive deficit in the rats, a finding successfully reproduced assessing the animals behavior in water T-maze for a prolonged period.

Results:

Relative to the controls, an increased number of the mistakes could be clearly evidenced in scopolamine and atropine treated rats. This cognitive deficit was abolished (obtained values were equal to control values) by subsequent coadministration of NaBPC157 (10 µg or 10 ng/kg b.w., i.p.).

Considering the widely implicated significance of these models for human cognitive function impairments, it is evident that NaBPC157 is useful in the therapy of cognitive disorders.

EXAMPLE 49

Effect on Withdrawal Disturbances

Materials, Methods and Results:

NaBPC157 exhibited an anti-convulsant effect interacting with the GABAergic system and improved the diazepam efficacy when coadministered (10 µg/kg, 10 ng/kg i.p.) with diazepam (5.0 mg/kg i.p., twice daily for 10 days). NaBPC157 attenuated diazepam tolerance and postponed the withdrawal effects and physical dependence. In tolerance assays forty-two hours after the conditioning regimen, shorter preconvulsive latencies than that in healthy mice following an isoniazid treatment (800 mg/kg i.p.) were observed if diazepam (5.0 mg/kg i.p.) was given again to mice previously conditioned with diazepam alone. This was completely avoided in animals conditioned with NaBPC157 (both doses) and diazepam. In a physical dependence assay (assessed at 6, 14, 42, and 72 hours after the conditioning treatment) shorter pre-convulsive latencies were noted in diazepam conditioned mice than in non-conditioned healthy mice following an isoniazid treatment forty-two and seventy-two hours after the conditioning treatment. NaBPC157 (10 µg/kg dose) combined with diazepam postponed this effect until the last observed interval. In this group at six hour intervals, unlike in diazepam conditioned mice, isoniazid preconvulsive latencies were still longer than in corresponding controls. NaBPC157 does not produce any tolerance effect.

Considering the significance of these models for human conditions, it is evident that NaBPC157 is useful in the therapy of the withdrawal disturbances.

EXAMPLE 50

The Effect on Kidney Disturbances

Materials and Methods:

Mercuric chloride (1 mg/kg i.v.) or cysplatinum (10 mg/kg s.c.) administration produces acute renal failure in experimental animals. When induced in this way, renal failure strongly correlates with corresponding human disturbance. Consequently, the lesions induced in rats share a considerably high degree of similarity with corresponding lesions in human patients.

Results:

NaBPC157 markedly attenuated the lesions in rats in both pre-treatment and post-treatment conditions. A unilateral nephrectomy produced a marked functional overload and a functional hypertrophy of the remaining kidney. NaBPC157 treatment increased diuresis in unilaterally nephrectomized animals and decreased the hypertrophy of the remaining kidney. Thus, in terms of the functional theory of compensatory renal hypertrophy, these findings strongly emphasize an improved function of the remaining kidney. This is also supported by additional biochemical results. In addition, these data are completely in line with the effects obtained in hypertensive rats with renal artery stenosis and/or unilateral nephrectomy. The useful application of NaBPC157 in the therapy of kidney disturbances is evident.

EXAMPLE 51

Cellular Immune Responses of Peripheral Blood Lymphocytes

Cellular immune responses of peripheral blood lymphocytes to BPC were investigated in the controls and in the patients with different diseases presented in Table 2. Peripheral blood T cell responses to BPC were tested by means of the method described by deSmet et al (deSmet MD et al. in: "Cellular immune responses of patients with uveitis to retinal antigens and their fragments." *Am. J. Ophthal.*, 110: 135–142,1990) with 7 day cell cultures. The cells were incubated without the antigen and with 20 ug /l of the antigen (BPC157 pentadecapeptide). For each patient the stimulation index was calculated by dividing the mean counts of the antigen stimulated cultures with the mean counts of the control cell cultures in which no antigen, i.e. BPC157 pentadecapeptide, was added. The results are presented in Table 2.

The control values of ≦2 measured in the control subjects (Table 2) corresponded to the values of other investigators for the peptides of similar molecular weight, i.e. no sensitization of peripheral blood lymphocytes to BPC157 pentadecapeptide was observed in the control subjects. In the patients with different diseases, marked cellular responses to BPC presented in Table 2 indicated systemic lymphocyte sensitization to this gastric juice peptide. These data clearly demonstrate the presence of BPC-related disturbances in patients suffering from apparently different diseases. This suggests the application of the BPC-related agents (e.g. the salts of the pentadecapeptide BPC157) in an immunomodulatory therapy of corresponding disturbances.

TABLE 2

Elevated stimulation indices of peripheral blood T cells in 11 patients with different diseases.

| DISEASE | SEX | STIMULATION INDEX control values < 2 |
|---|---|---|
| PEPTIC ULCER | F | 26.82 |
| MULTIPLE SCLEROSIS | F | 13.80 |
| SUBACUTE SCLEROSANS PANCENCEPHALITIS | F | 2.54 |
| OPTIC NEURITIS | M | 3.54 |
| OPTIC NEURITIS | F | 9.53 |
| UVEITIS | F | 16.87 |
| UVEITIS | M | 15.21 |
| UVEITIS | F | 22.30 |
| SERONEGATIVE SPONDYLOARTHROPAPATHY | F | 4.99 |
| HEREDITARY EOSINOPHILIA AND BULLOUS DERMATITIS | F | 2.70 |
| UVEITIS | F | 4.75 |

The results of the above described pharmacological investigations demonstrate the advantageous activity of the salts of the BPC peptides in protecting organisms against stress and diseases and, in general, normalizing the organic functions. The peptide salts of the present invention are also effective for the prevention and therapy of several human and/or animal diseases and disorders.

What is claimed is:

1. A salt of a Body Protection Compound peptide (BPC) comprising 8 amino acid residues wherein the anion of the salt is a negatively charged peptide having the general formula

[Zaa Pro Pro Pro Xaa Yaa Pro Ala] (SEQ ID NO: 1)$^{(-) \text{ or } (2-)}$ wherein Xaa is a neutral aliphatic amino acid residue, Yaa is a basic amino acid residue and Zaa is an acidic amino acid residue and wherein the cation of the salt is the cation of an inorganic or organic non-toxic base.

2. That salt according to claim 1 wherein the cation is selected from the group consisting of alkali metals, alkaline earth metals, $Zn^{-2+}$, primary, secondary and tertiary amines.

3. The salt according to claim 1 wherein

Xaa is Ala, bAla, Leu, Iee, Gly, Val, Nle or Nva,

Yaa is Lys, Arg, Orn or His and

Zaa is Glu, Asp, Aad or Apm.

4. The salt according to claim 1, which furthermore comprises a pharmaceutically or diagnostically acceptable carrier.

5. The salt according to claim 1, which furthermore comprises trehalose.

6. The salt according to claim 1 wherein the general formula is Xaa Zaa Pro Pro Pro Xaa Yaa Pro Ala Asp Zaa Ala Xaa Xaa Xaa (SEQ ID NO: 2).

7. The salt according to claim 1 wherein the peptide is selected from the group consisting of:

Leu Glu Pro Pro Pro Gly Lys Pro Ala Asp Asp Ala Leu Gly Val (SEQ ID NO: 3);

Gly Glu Pro Pro Pro Gly Lys Pro Ala Asp Asp Ala Gly Leu Val (SEQ ID NO: 4);

Leu Glu Pro Pro Pro Leu Lys Pro Ala Asp Asp Ala Leu Gly Val (SEQ ID NO: 5);

Leu Glu Pro Pro Pro Leu Lys Pro Ala Asp Ala Leu Gly Val (SEQ ID NO: 6);

Gly Glu Pro Pro Pro Gly Lys Pro Ala Asp Ala Gly Leu Val (SEQ ID NO: 7);

Glu Pro Pro Pro Leu Lys Pro Ala (SEQ ID NO: 8)

Asp Pro Pro Pro Ile Arg Pro Ala Asp (SEQ ID NO: 9);

Glu Pro Pro Pro Leu Lys Pro Ala Asp (SEQ ID NO: 10);

Leu Glu Pro Pro Pro Leu Lys Pro Ala Asp Ala Leu Gly Val (SEQ ID NO: 11);

Gly Glu Pro Pro Pro Gly Arg Pro Ala Asp (SEQ ID NO: 12); and

Glu Pro Pro Pro Leu Lys Pro Ala Asn (SEQ ID NO: 13).

8. The salt according to claim 1 wherein the peptide is cyclized.

9. The salt according to claim 1, wherein the salt is dissolved in an aqueous or aqueous/alcoholic solution.

10. A compatible, storage-stabel, pharmaceutical composition comprising a pharmaceutically effective amount of the BPC peptide salt according to claim 1, and optionally a physiologically acceptable carrier.

11. The pharmaceutical composition according to claim 10 further comprising trehalose.

12. A diagnostic storage-stable composition comprising a diagnostically effective amount of the BPC peptide salt according to claim 1.

13. A method of treating
disturbances connected with either nitric oxide (NO) formation or impaired NO-system functions in a subject comprising administering to said subject a pharmaceutically effective amount of a pharmaceutical composition, wherein said pharmaceutical composition comprises a pharmaceutically effective amount of a Body Protection Compound peptide salt (BPC) and optionally a physiologically acceptable carrier,
wherein said BPC comprises 8 amino acid residues wherein the anion of the salt is a negatively charged peptide having the general formula Zaa Pro Pro Pro Xaa Yaa Pro Ala (SEQ ID NO: 1)$^{(-) \; or \; (2-)}$ wherein
Xaa is a neutral aliphatic amino acid residue,
Yaa is a basic amino acid residue and
Zaa is an acidic amino acid residue
and wherein the cation of the salt is the cation of an inorganic or organic non-toxic base.

14. A method of cyto-protecting and organo-protecting a body comprising administering to said body a pharmaceutically effective amount of a pharmaceutical composition, wherein said pharmaceutical composition comprises a pharmaceutically effective amount of a Body Protection Compound peptide salt (BPC) and optionally a physiologically acceptable carrer,
wherein said BPC comprises 8 amino acid residues wherein the anion of the salt is a negatively charged peptide having the general formula Zaa Pro Pro Pro Xaa Yaa Pro Ala (SEQ ID NO: 1)$^{(-) \; or \; (2-)}$ wherein
Xaa is a neutral aliphatic amino acid residue.
Yaa is a basic amino acid residue and
Zaa is an acidic amino acid residue
and wherein the cation of the salt is the cation of an inorganic or organic non-toxic base.

15. A process for the preparation of the BPC peptide salt according to claim 1 comprising mixing at least one Body Protection Compound peptide in an aqueous or aqueous/alcoholic solvent with one or more bases and obtaining a Body Protection Compound peptide salt wherein the cation of the salt is the cation of an inorganic or organic non-toxic base.

16. The salt of claim 1 wherein the cation is selected from the group consisting of $Na^+$, $K^+$, $Li^+$, $Cs^+$, $Ca^{2+}$, $NH_4^+$, triethanolamine$^+$, cyclohexylamine$^+$, 2-AMP$^+$ (2-amino-1-propanol) and Tris-(hydroxymethyl)-aminomethane.

17. The salt of claim 8 wherein the peptide is cyclized by an amide bond between the first and the last amino acid residue.

18. The salt of claim 9 wherein the aqueous or aqueous/alcoholic solution has a pH of 6.0 to 8.5.

19. The method of claim 13, wherein the disturbances connected with either nitric oxide (NO) formation or impaired NO-system functions are selected from the group consisting of hypertension, angina, impotence, circulatory and septic shock, stroke, inflammation, respiratory distress syndrome, adhesion and aggregation of platelets and leukocytes, endothelial dysfunction, gastrointestinal lesions, peristalsis disturbances, diabetes pancreatitis, hypotension and Parkinson's disease.

20. A method of using the pharmaceutical composition of claim 10 to treat dysfunctions or hyperfunctions of somatosensory nerves.

21. The method of claim 20, wherein the dysfunctions or hyperfunctions of somatosensory nerves are selected from the group consisting of sensory neuropathy, postherpetic neuralgia, atopic dermatitis, impaired healing of injured tissue, acquired cold and heat urticaria, psoriasis, bullous pemphigoid, eczema, photodermatoses, chronic arthritis, gastrointestinal lesions, specific or non-specific hyperreactivity of upper and lower respiratory tracts, asthma, and rhinitis.

22. A method of using the pharmaceutical composition of claim 10 to treat endothelium disturbances.

23. A method of using the pharmaceutical composition of claim 10 to treat wounds or ulcers.

24. A method of using the pharmaceutical composition of claim 10 to treat conditions relating to acute and/or chronic inflammation.

25. The method of claim 24, wherein the conditions relating to acute and/or chronic inflammation are selected from the group consisting of chronic arthritis, disorders related with delayed type of hypersensitivity, and gastrointestinal lesions.

26. A method of using the pharmaceutical composition of claim 10 to treat liver disorders, organ lesions induced by free radicals, organ lesions induced by irritation.

27. A method of using the pharmaceutical composition of claim 10 to treat disorders connected with cathecholaminergic system disturbances.

28. The method of claim 27, wherein the disorders connected with cathecholaminergic system disturbances are selected from the group consisting of schizophrenia, amphetamine challenge effects and drug abuse.

29. A method of using the pharmaceutical composition of claim 10 to treat a disorder selected from the group consisting of stress related conditions, acute pancreatitis; acute pancreatitis with concomitant gastroduodenal pathology, cardiac disturbances, depressive disturbances, Parkinson's disease, Parkinson's disease-like pathology, temperature disturbances, bone impairments, hypertension-induced various organ damages, disturbances of coagulation, pain disturbances, convulsion disorders, spinal cord injury, alcohol injuries induced by alcohol abuse or increased alcohol intake, brain ischemic disorders, peripheral nerve injuries, cataleptic disorders and neuroleptic disturbances, disorders related to abnormal or mutant lymphocytes, disturbances of fetuses, vaginal atrophy caused by ovariectomy conditions, osteoporosis development caused by ovariectomy conditions, tumors, viral diseases, AIDS, ARC, gastrointestinal lesions, cognitive disorders, withdrawal disturbances, kidney disturbances and disturbances in cellular immune response.

* * * * *